United States Patent [19]

Hefner, Jr. et al.

[11] Patent Number: 5,364,912

[45] Date of Patent: Nov. 15, 1994

[54] THERMOPLASTIC RESINS FROM POLYGLYCIDYL ESTERS CONTAINING MESOGENIC MOIETIES

[75] Inventors: Robert E. Hefner, Jr.; Jimmy D. Earls, both of Lake Jackson, Tex.

[73] Assignee: The Dow Chemical Company, Midland, Mich.

[21] Appl. No.: 107,267

[22] Filed: Aug. 16, 1993

Related U.S. Application Data

[63] Continuation-in-part of Ser. No. 905,592, Jun. 26, 1992, abandoned, which is a continuation-in-part of Ser. No. 582,048, Sep. 13, 1990, abandoned.

[51] Int. Cl.$^5$ ............... C08G 59/12; C08G 59/22; C08G 59/42; C08G 59/64
[52] U.S. Cl. ............... 525/418; 525/449; 525/523; 525/524; 525/525; 525/526; 525/527; 525/528; 525/530; 525/533; 528/87; 528/96; 528/97; 528/98; 528/99; 528/102; 528/220; 528/361; 528/365; 549/555
[58] Field of Search ............... 525/530, 523, 524, 525, 525/526, 527, 418, 449, 528, 530, 533; 528/365, 361, 87, 96, 97, 98, 99, 102, 220, 361, 365; 549/557

[56] References Cited

U.S. PATENT DOCUMENTS

| | | | |
|---|---|---|---|
| 2,895,947 | 7/1959 | Shokal et al. | 549/557 |
| 3,073,803 | 1/1963 | Raecke et al. | |
| 3,477,990 | 11/1969 | Dante et al. | 525/523 |
| 3,714,198 | 1/1973 | Metzger et al. | |
| 4,107,116 | 8/1978 | Riew | 525/530 |
| 4,540,802 | 9/1985 | Tomita et al. | 549/557 |
| 4,667,044 | 5/1987 | Nees et al. | 549/557 |

FOREIGN PATENT DOCUMENTS

| | | |
|---|---|---|
| 0361852 | 4/1990 | European Pat. Off. |
| 0379058 | 7/1990 | European Pat. Off. |
| 1360811 | 7/1974 | United Kingdom |
| 1516452 | 7/1978 | United Kingdom |
| 1542709 | 3/1979 | United Kingdom |

OTHER PUBLICATIONS

Patent Abstracts of Japan, vol. 12, No. 209, (15 Jun. 1988) & JP-A-63 010 617.
Patent Abstracts of Japan, vol. 15, No. 104, (13 Mar. 1991) & JP-A-03 002 261.
CA97(2)6812r & CA96(26):218245n equivalents for Covegno Italiano di Scienze Delle Macromolecole, No. 5, 1981 pp. 239–242 Schleier et al.
European Polymer Journal, vol. 21, No. 3, 1985, pp. 259–264, F. Cser et al.
*Journal of Applied Polymer Science*, vol. 11, pp. 465–471 (1967), "Evaluation of Polyglycidyl Esters as Cryogenic Adhesives by Sandler".
*Tetrahedron*, vol. 41, pp. 763–768 (1985), "New Glycidyl Ester Compounds Containing a Performed Imide Ring-1" by Serra et al.
*Proceedings of the Second Symposium on Polymeric Crystals*, pp. 2 3 (1983), "Polymeric Liquid Crystals by Blumstein".
*Polymer Liquid Crystals*, "Low MW Liquid Crystals-Structure/Property Relations" (1982) pp. 5 17, by Ciferri et al.
*Encyclopedia Reprint Series*, "High Performance Polymers and Composites", (1991), pp. 466, 470, 476, by Kroschwitz.
*ACS Symposium Series 435*, "Liquid-Crystalline Polymers", (1989), p. 2 by Weiss et al.
*Hawley's Condensed Chemical Dictionary*, 11th Edition, p. 898 (1987), "Phenolsulfonic Acid" by Sax et al.
*Encyclopedia of Polymer Science and Technology*, vol. 10, pp. 116–119 (1969), "Phenoxy Resins" by John Wiley and Sons.

*Primary Examiner*—John C. Bleutge
*Assistant Examiner*—D. R. Wilson

[57] ABSTRACT

Thermoplastic resins are prepared by reacting polyglycidyl esters containing one or more mesogenic moieties with compounds having an average of more than one active hydrogen atom per molecule. These resins exhibit ordering of the molecular chains in the melt phase and are susceptible to orientation during processing which can result in enhanced unidirectional mechanical properties. These resins are useful in coatings, laminates, castings and the like.

4 Claims, No Drawings

THERMOPLASTIC RESINS FROM POLYGLYCIDYL ESTERS CONTAINING MESOGENIC MOIETIES

CROSS-REFERENCE TO RELATED APPLICATIONS

This application is a continuation-in-part of application Ser. No. 07/905,592 filed Jun. 26, 1992 (now abandoned) which is a continuation-in-part of application Ser. No. 07/582,048 filed Sep. 13, 1990, now abandoned, all of which are incorporated herein by reference in their entirety.

FIELD OF THE INVENTION

The present invention concerns glycidyl esters of mono and polycarboxylic acids containing one or more mesogenic moieties, thermoplastic resin compositions, curable compositions and cured compositions thereof.

BACKGROUND OF THE INVENTION

Glycidyl esters of polycarboxylic acids are a specialized class of thermosettable resins with utility in a myriad of applications, notably coatings, adhesives, encapsulants, moldings, laminates, castings, electrical insulation, weatherable coatings, sealants, impregnants, plasticizers, fibers, foams, and the like. The art describes numerous incremental improvements in the physical, mechanical, thermal and/or chemical resistant properties possessed by certain polyglycidyl esters relative to their polyglycidyl ether counterparts. This nonwithstanding, substantial room for improvement in one or more of the aforesaid properties of polyglycidyl esters is desireable for each of the aforementioned applications.

The present invention provides a method for improving the properties of mono and polyglycidyl esters as well as the curable and cured compositions thereof by incorporating one or more mesogenic moieties into the backbone chain of said glycidyl esters. These glycidyl esters exhibit ordering of the molecular chains in the melt phase and/or in the advanced compositions thereof. This morphology is susceptible to orientation during processing which can result in enhanced unidirectional mechanical properties. This is not possible to any significant extent with the conventional (non-mesogenic) glycidyl esters. The mesogenic structures incorporated into the backbone chain of the glycidyl esters and the polymer chains of the resultant polymers thereof are believed to be responsible for the improvement in properties.

SUMMARY OF THE INVENTION

One aspect of the present invention pertains to polyglycidyl esters containing one or more mesogenic moieties represented by the following Formula I

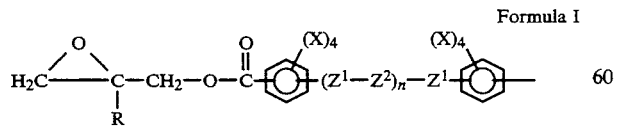

Formula I

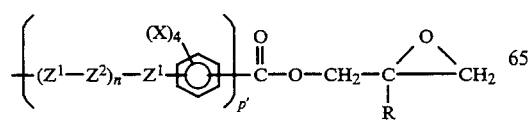

wherein at least about 80 percent of the $-(Z^1-Z^2)_n-Z^1-$ linkages and the glycidyl ester groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), $-NO_2$, or $-C\equiv N$; each $Z^1$ is independently a direct single bond, $-CR^1=CR^1-$, $-CR^1=CR^1-CR^1=CR^1-$, $-CR^1=N-N=CR^1-$, $-CR^1=CR^1-CO-O-(CHR^1)_{p'}-$, $-CR^1=CR^1-O-CO-(CHR^1)_{p'}-$, $-(CHR^1)_{p'}-O-CO-CR^1=CR^1-$, $-(CHR^1)_{p'}-CO-O-CR^1=CR^1-$, $-CR^1=CR^1-CO-O-$, $-O-CO-CR^1=CR^1-$, $-CO-NR^1-$, $-NR^1-CO-$, $-CO-NR^1-NR^1-CO-$, $-C\equiv C-$, $-C\equiv C-C\equiv C-$, $-CO-S-$, $-S-CO-$, $-CR^1=N^1-$, $-N=CR^1-$, $-O-CO-$, $-CO-O-$, $-CR^1=CR^1-CO-$, $-CO-CR^1=CR^1-$, $-CR^1=CR^1-O-CO-$, $-CO-O-CR^1=CR^1-$, $-CH_2-CH_2-CO-O-$, $-O-CO-CH_2-CH_2-$, $-N=N-$,

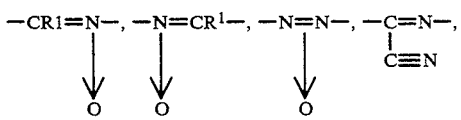

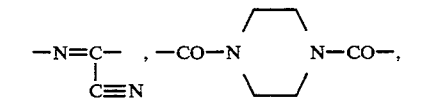

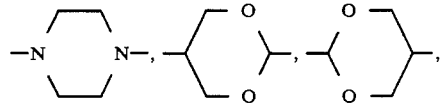

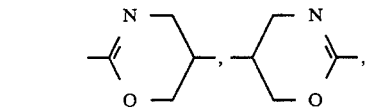

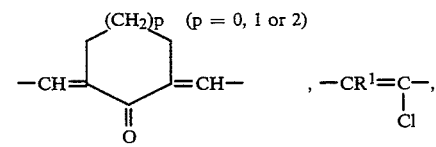

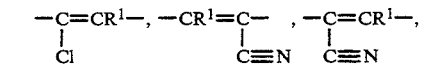

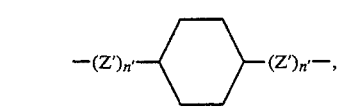

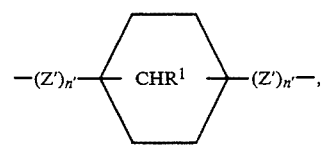

-continued

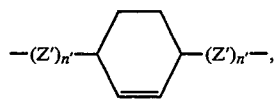

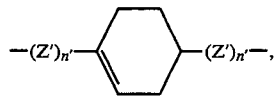

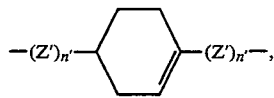

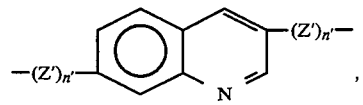

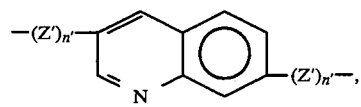

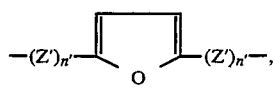

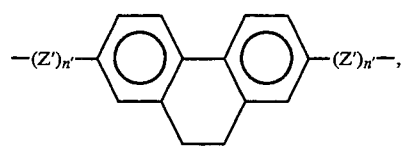

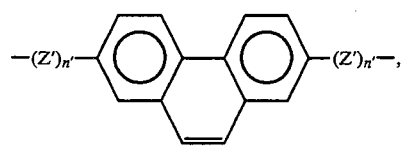

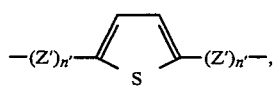

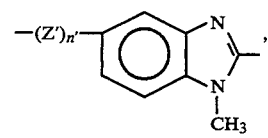

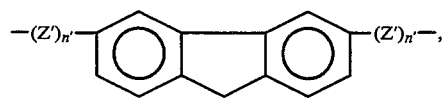

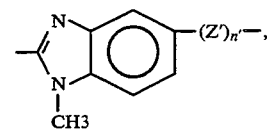

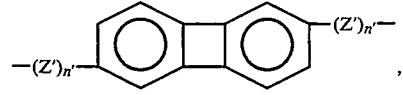

-continued

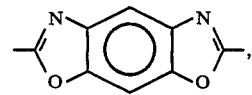

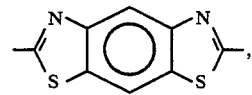

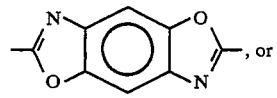, or

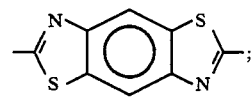;

$Z^2$ is a group represented by a cyclic or bicyclic ring system containing from 5 to about 12 carbon atoms and can be cycloaliphatic, polycycloaliphatic, aromatic or a combination thereof; n is 0 to 2; p' is 1 or 2; p" has a value of zero to 100; each Z' is independently a —CO—, —O—CO—, —CO—O—, —CO—NR$^1$— or —NR$^1$—CO— group and each n' independently has a value of zero or one; with the proviso that the polyglycidyl ester of Formula I is not the polyglycidyl ester of 4,4'-dicarboxystilbene (R is H, X is H, n=O, p"=O, $Z^1$ is —CR$^1$=CR$^1$— wherein both R$^1$ groups are H) or the polyglycidyl ester or polymethylglycidyl ester of bis(4'-carboxyphenyl)-1,4-benzenediimine (R is H or CH$_3$, X is H, n=1, p"=O, $Z^1$ is —CR$^1$=N$^1$— wherein R$^1$ is H and $Z^2$ is

Another aspect of the present invention pertains to polyglycidyl esters containing one or more mesogenic moieties represented by the following Formula II

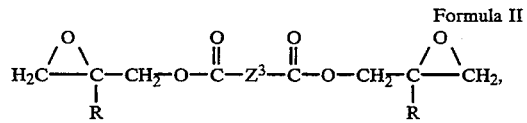

Formula II wherein $Z^3$ is

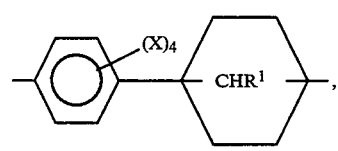

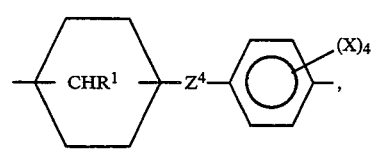

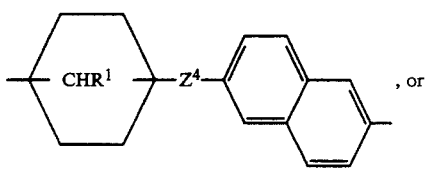, or

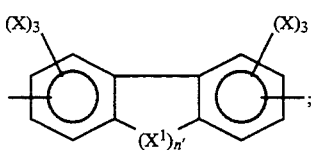

and $Z^4$ is —CO—O—, —O—CO—, —NR$^1$—CO— or —CO—NR$^1$—; $X^1$ is a divalent hydrocarbyl group having from 1 to about 10, preferably from 1 to about 4, carbon atoms which can contain one or more heteroatoms selected from N, O, S and the like and can be saturated or unsaturated; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and n' is zero or one.

Another aspect of the present invention pertains to monoglycidyl ester compounds containing one or more mesogenic moieties represented by the following Formula III

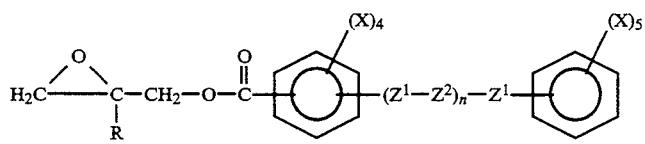

Formula III wherein at least about 80 percent of the —($Z^1$-$Z^2$)$_n$—$Z^1$— linkages and the glycidyl ester groups are in the para position with respect to each other; R, $R^1$, X, $Z^1$, $Z^2$, Z', n, p' and n' are as hereinbefore defined; with the proviso that the monoglycidyl ester of Formula III is not the monoglycidyl ester of 4-carboxybiphenyl (R=H, X=H, n=0, $Z^1$=a direct single bond).

Another aspect of the present invention pertains to monoglycidyl ester compounds containing one or more mesogenic moieties represented by the following Formula IV

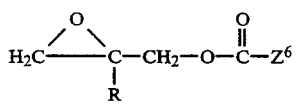

Formula IV wherein R, $R^1$, X, $X^1$, $Z^3$, $Z^4$ and n' are as hereinbefore defined and $Z^6$ is

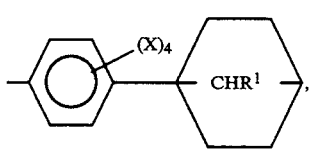

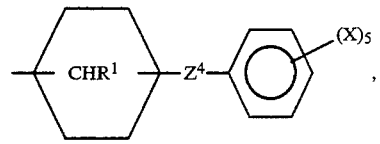,

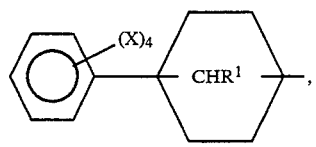,

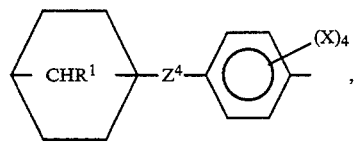,

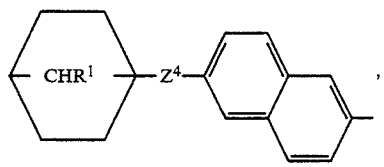,

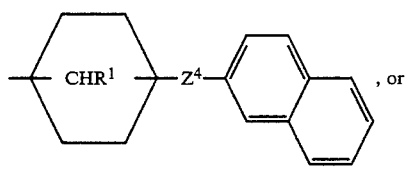, or

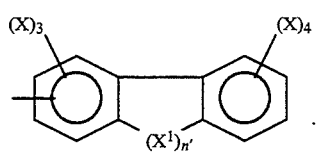.

Another aspect of the present invention pertains to advanced polyglycidyl ester compositions prepared by reacting (A) one or more of the polyglycidyl esters containing one or more mesogenic moieties, said polyglycidyl esters being those represented by either Formula I, with the proviso that the polyglycidyl ester of Formula I can include the polyglycidyl ester of 4,4'-dicarboxystilbene or the polyglycidyl ester or polymethylglycidyl ester of bis(4'-carboxyphenyl)-1,4-benzendiimine; or Formula II; with (B) at least one compound having an average of more than one active hydrogen atom per molecule; and wherein components (A) and (B) are employed in quantities which provide a ratio of active hydrogen atoms per epoxide group of from about 0.01:1 to about 0.95:1, more suitably from about 0.05:1 to about 0.8:1, most suitably from about 0.1:1 to about 0.5:1.

Another aspect of the present invention pertains to thermoplastic resin compositions prepared by the advancement reaction of (A) one or more of the polyglycidyl esters containing one or more mesogenic moieties, said polyglycidyl esters being those represented by either Formula I, with the proviso that the polyglycidyl ester of Formula I can include the polyglycidyl ester of 4,4'-dicarboxystilbene or the polyglycidyl ester or polymethylglycidyl ester of bis(4'-carboxyphenyl)-1,4-benzenediimine; or Formula II with B) at least one compound having an average of more than one active hydrogen atom per molecule; and wherein components (A) and (B) are employed in quantities which provide a ratio of active hydrogen atoms per epoxide group of from about 0.96:1 to about 1.05:1.

Another aspect of the present invention pertains to blends of (A) one or more of the polyglycidyl esters or monoglycidyl ester compounds containing one or more mesogenic moieties which polyglycidyl esters or monoglycidyl ester compounds are represented by the aforementioned of Formula I can include the polyglycidyl ester of 4,4'-dicarboxystilbene or the polyglycidyl ester or polymethylglycidyl ester of bis(4'-carboxyphenyl)-1,4-benzenediimine and the monoglycidyl ester of Formula III can include the monoglycidyl ester of 4-carboxybiphenyl; and (B) one or more polyepoxides represented by the following Formulas V, VI, VII, VIII, IX, X or XI;

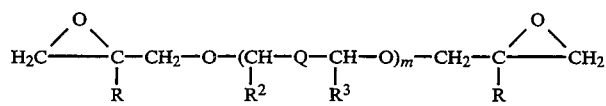

Formula V

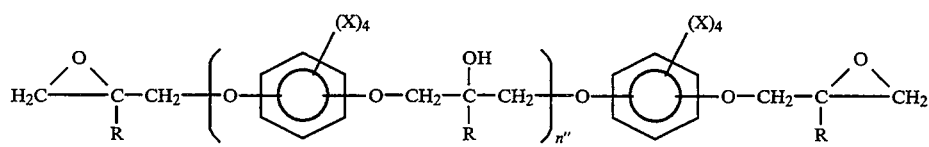

Formula VI

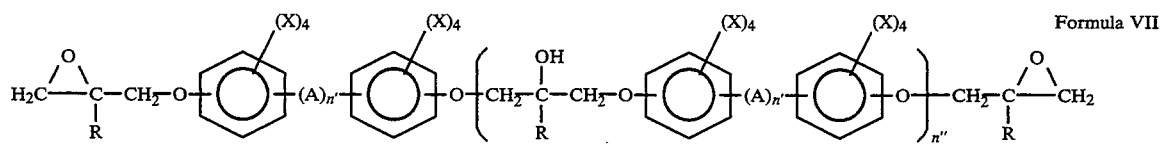

Formula VII

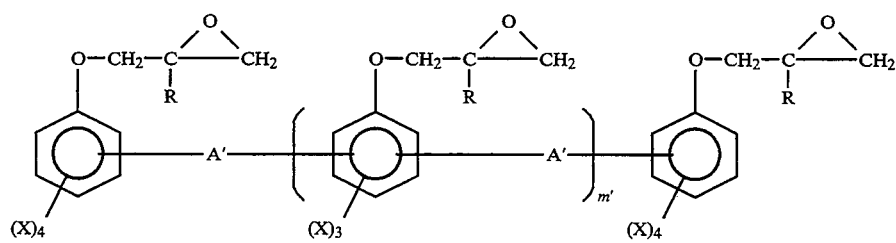

Formula VIII

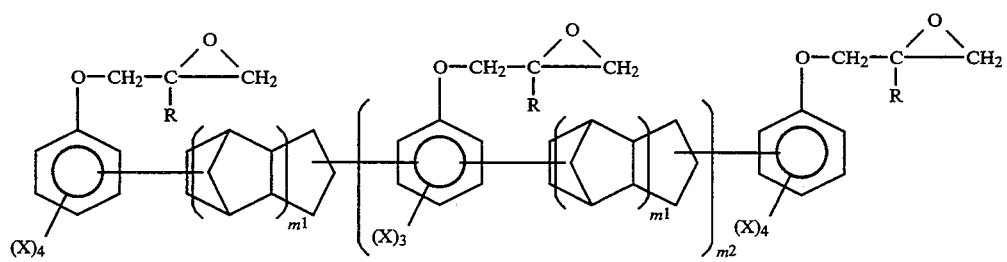

Formula IX

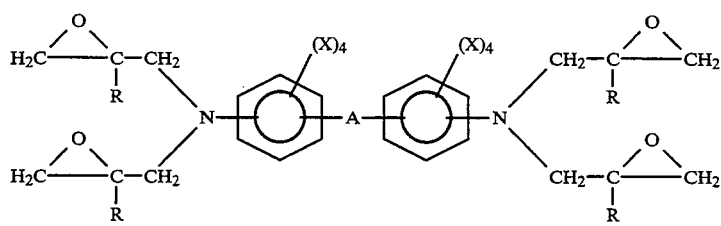

Formula X

Formula XI

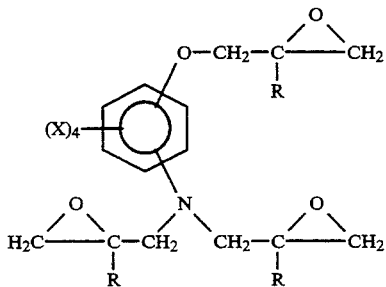

wherein each A is independently a divalent hydrocarbyl group having from 1 to about 12, preferably from about 1 to about 6, more preferably from 1 to about 3, carbon atoms, —O—, —S—, —S—S—, —SO—, —SO$_2$—, or —CO—; each A' is independently a divalent hydrocarbon group having from 1 to about 6, preferably from 1 to about 3, carbon atoms; Q is a single bond, —CH$_2$—S—CH$_2$—, —(CH$_2$)$_{n^1}$—, or

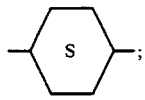

each R is independently hydrogen or an alkyl group having from 1 to about 4 carbon atoms; each R$^2$ and R$^3$ is independently hydrogen, a hydrocarbyl or halohydrocarbyl group having from 1 to about 6, preferably from 1 to about 3, more preferably from 1 to about 2, carbon atoms; each X is independently hydrogen, a hydrocarbyl or hydrocarbyloxy group having from 1 to about 12, preferably from about 1 to about 6, most preferably from 1 to about 4, carbon atoms, a halogen atom, —NO$_2$ or —C≡N; m has a value from about 1 to about 10, preferably from about 1 to about 4, more preferably from about 1 to about 2; m' has an average value from about 0.01 to about 12, preferably from about 1 to about 6, more preferably from about 1 to about 3; m$^1$ has an average value from about 1 to about 12, preferably from about 1 to about 6, more preferably from about 1 to about 3; m$^2$ has a value from about 1 to about 12, preferably from about 2 to about 6, more preferably from about 2 to about 3; n' has a value of zero or 1; n" has an average value from about zero to about 3, preferably from about zero to about 1.5, more preferably from about zero to about 0.5, and n$^1$ has an average value from about 1 to about 10; and wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

Another aspect of the present invention pertains to blends of (A) one or more of the advanced polyglycidyl esters containing one or more mesogenic moieties which advanced polyglycidyl esters are prepared by reacting one or more polyglycidyl esters represented by Formulas I or II, with the proviso that the polyglycidyl ester of Formula I can include the polyglycidyl ester of 4,4'-dicarboxystilbene or the polyglycidyl ester or polymethylglycidyl ester of bis(4'-carboxyphenyl)-1,4-benzenediimine, and at least one compound having an average of more than one active hydrogen atom per molecule; and (B) one or more polyepoxides represented by Formulas V, VI, VII, VIII, IX, X or XI; and wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

Another aspect of the present invention pertains to curable compositions comprising at least one polyglycidyl ester containing one or more mesogenic moieties represented by Formula I and a curing amount of a suitable curing agent therefor.

Another aspect of the present invention pertains to curable compositions comprising at least one polyglycidyl ester containing one or more mesogenic moieties represented by Formula II and a curing amount of a suitable curing agent therefor.

Another aspect of the present invention pertains to curable compositions comprising (A) at least one polyglycidyl ester containing one or more mesogenic moieties, said polyglycidyl ester being represented by either Formula I, with the proviso that the polyglycidyl ester of Formula I can include the polyglycidyl ester of 4,4'-dicarboxystilbene or the polyglycidyl ester or polymethylglycidyl ester of bis(4'-carboxyphenyl)-1,4-benzenediimine; or Formula II;

(B) at least one of the aforementioned monoglycidyl ester compounds containing one or more mesogenic moieties, said monoglycidyl ester compounds being represented by Formulas III or IV, with the proviso that the monoglycidyl ester of Formula III can include the monoglycidyl ester of 4-carboxybiphenyl, and (C) a curing amount of a suitable curing agent therefor; wherein component (A) is present in an amount suitably from about 1 to about 99, more suitably from about 50 to about 90, most suitably from about 70 to about 90, percent by weight based upon the combined weight of components (A) and (B) and component (B) is present in an amount suitably from about 99 to about 1, more suitably from about 50 to about 10, most suitably from about 30 to about 10, percent by weight based upon the combined weight of components (A) and (B).

Another aspect of the present invention pertains to curable compositions comprising (A) an advanced polyglycidyl ester resulting from reacting
  (1) at least one of the polyglycidyl esters containing one or more mesogenic moieties, said polyglycidyl esters being those represented by either Formula I, with the proviso that the polyglycidyl ester of Formula I can include the polyglycidyl ester of 4,4'-dicarboxystilbene or the polyglycidyl ester or polymethylglycidyl ester of bis(4'-carboxyphenyl)-1,4-benzenediimine; or Formula II; with
  (2) at least one compound having an average of more than one active hydrogen atom per molecule; wherein components (A1) and (A2) are employed in quantities which provide a ratio of active hydrogen atoms to epoxide groups suitably from about 0.01:1 to about 0.95:1, more suitably from about 0.05:1 to about 0.8:1, most suitably from about 0.1:1 to about 0.5:1; and
(B) a curing amount of a suitable curing agent for component (A).

Another aspect of the present invention pertains to curable compositions comprising a blend of
(A) at least one of the polyglycidyl esters or monoglycidyl ester compounds containing one or more mesogenic moieties represented by Formulas I or II, with the proviso that the polyglycidyl ester of Formula I can include the polyglycidyl ester of 4,4'-dicarboxystilbene or the polyglycidyl ester or polymethylglycidyl ester of bis(4'-carboxyphenyl)-1,4-benzenediimine; or by the aforementioned Formulas III or IV with the proviso that the monoglycidyl ester of Formula III can include the monoglycidyl ester of 4-carboxybiphenyl;
(B) at least one of the polyepoxide resins represented by Formulas V, VI, VII, VIII, IX, X or XI; and
(C) a curing amount of a suitable curing agent therefor; wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

Another aspect of the present invention pertains to curable compositions comprising a blend of
(A) at least one of the advanced polyglycidyl esters containing one or more mesogenic moieties prepared by reacting
  (1) one or more polyglycidyl esters represented by Formulas I or II, with the proviso that the polyglycidyl ester of Formula I can include the polyglycidyl ester of 4,4'-dicarboxystilbene or the polyglycidyl ester or polymethylglycidyl ester of bis(4'-carboxyphenyl)-1,4-benzenediimine; with
  (2) at least one compound having an average of more than one active hydrogen atom per molecule; wherein components (1) and (2) are employed in quantities which provide a ratio of active hydrogen atoms per epoxide group suitably from about 0.01:1 to about 0.95:1, more suitably from about 0.05:1 to about 0.8:1, most suitably from 0.1:1 to about 0.5:1;
(B) at least one of the polyepoxide resins represented by Formulas V, VI, VII, VIII, IX, X or XI; and
(C) a curing amount of a suitable curing agent therefor; wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

A further aspect of the present invention pertains to products resulting from curing the aforementioned curable compositions.

A further aspect of the present invention pertains to products resulting from the application of an electric field or magnetic field or drawing and/or shear forces before and/or during curing or processing of the aforementioned compositions.

A still further aspect of the present invention pertains to products resulting from the application of an electric field or magnetic field or drawing and/or shear forces before and/or during curing or processing of a curable composition comprising
(A) at least one polyglycidyl ester containing one or more mesogenic moieties said polyglycidyl esters being those represented by Formulas I or II, with the proviso that the polyglycidyl ester of Formula I can include the polyglycidyl ester of 4,4'-dicarboxystilbene or the polyglycidyl ester or polymethylglycidyl ester of bis(4'-carboxyphenyl)-1,4-benzenediimine; and
(B) a curing amount of at least one suitable curing agent for component (A).

The term "mesogenic" as is used herein designates compounds containing one or more rigid rodlike structural units which have been found to favor the formation of liquid crystal phases in the case of low molar mass substances. Thus the mesogen or mesogenic moiety is that structure responsible for molecular ordering. The term "mesogenic" is further defined by R. A. Weiss (ed.) and C. K. Ober (ed.) in *Liquid-Crystalline Polymers*, ACS Symposium Series 435 (1989) on page 2: "The rigid unit responsible for the liquid crystalline behavior is referred to as the mesogen," and "Liquid crystalline order is a consequence solely of molecular shape anisotropy, such as found in rigid rod-shaped molecules . . . ". Further definition of the term "mesogenic" can be found in *Polymeric Liquid Crystals*, Alexandre Blumstein (ed.), (1983) on pages 2-3 and in *Polymeric Liquid Crystals*, A. Ciferri, W. R. Krigbaum and Robert B. Meyer (eds.) (1982) on pages 5-9, both of which are incorporated herein by reference.

DETAILED DESCRIPTION OF THE INVENTION

The mono and polyglycidyl ester compositions of the present invention can be prepared by any suitable method known to those skilled in the art. Suitable such methods include, for example, the following:

A. Reaction of a mono or polycarboxylic acid (or ester thereof) and an epihalohydrin to form the corresponding halohydrin ester of said mono or polycarboxylic acid followed by dehydrohalogenation of the resultant mono or polyhalohydrin ester. Exemplary of this method are the teachings found in U.S. Pat. Nos. 2,895,947; 2,476,922; 2,224,026, as well as British Patent No. 1,360,811.

B. Reaction of a salt, typically an alkali metal salt, of a mono or polycarboxylic acid and an epihalohydrin, typically epichlorohydrin. Details concerning this reaction are delineated in U.S. Pat. Nos. 2,781,333; 2,801,232 and 3,073,803.

C. Reaction of a mono or polycarboxylic acid halide and glycidol in the presence of a base, especially an organic tertiary amine. Details concerning this reaction are delineated in U.S. Pat. Nos. 2,865,897 and 3,073,803, as well as by Sandler in *J. Chem. Eng. Data* Vol. II, No. 3, pages 447–448 (1966).

D. Epoxidation of allyl esters of mono or polycarboxylic acids with peroxy compounds, especially organic peracids. Examples of this reaction method are found in British Patent No. 862,588 and European Patent Application (published) No. 0,008,112.

E. Transesterification of mono or polycarboxylic acid esters with glycidol in the presence of a catalyst. Exemplary of this method are the teachings found in U.S. Pat. No. 4,667,044 and British Patent No. 1,516,452.

F. Transesterification of mono or polycarboxylic acid esters with carboxylic acid glycidyl esters in the presence of a catalyst. Exemplary of this method are the teachings found in British Patent No. 1,542,709.

All of the aforementioned references are incorporated herein in their entirety.

In the preparation of the mono or polyglycidyl ester of a mono or polycarboxylic acid, the carboxylic acid containing compound is typically reacted with an epihalohydrin in the presence of a suitable catalyst and in the presence or absence of a suitable solvent at a temperature suitably from about 0° C. to about 150° C., more suitably from about 20° C. to about 100° C., most suitably from about 40° C. to about 80° C.; at pressures suitably from about 30 mm Hg vacuum to about 100 psia., more suitably from about 65 mm Hg vacuum to about 50 psia., most suitably from about atmospheric pressure to about 20 psia.; and for a time sufficient to complete the reaction, usually from about 1 to about 48, more usually from about 1 to about 12, most usually from about 1 to about 6 hours. This initial reaction unless the catalyst is an alkali metal or alkaline earth metal hydroxide employed in stoichiometric quantities produces a halohydrin intermediate which is then reacted with a basic acting compound to convert the vicinal halohydrin groups to epoxide groups. Reaction of the halohydrin intermediate and basic acting compounds in the presence or absence of a suitable solvent is typically conducted at a temperature suitably from about 0° C. to about 100° C., more suitably from about 20° C. to about 80° C., most suitably from about 25° C. to about 60° C.; at pressures suitably from about 30 mm Hg vacuum to about 100 psia., more suitably from about 45 mm Hg vacuum to about 50 psia., most suitably from about 60 mm Hg vacuum to atmospheric pressure; and for a time sufficient to complete the dehydrohalogenation reaction, usually from about 15 minutes to about 12 hours, more usually from about 30 minutes to about 6 hours, most usually from about 1 hour to about 4 hours. The resultant product is a glycidyl ester compound.

Suitable epihalohydrins which can be employed to prepare the mono and polyglycidyl esters of the present invention include, for example, those represented by the following Formula XII

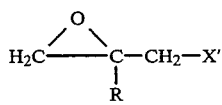

Formula XII wherein R is as previously defined; and X' is a halogen. Particularly suitable such epihalohydrins include, for example, epichlorohydrin, epibromohydrin, epiiodohydrin, methylepichlorohydrin, methylepibromohydrin, methylepiiodohydrin, combinations thereof and the like.

Suitable carboxylic acid containing compounds which can be employed to prepare the mono and polyglycidyl esters of the present invention include, for example, those represented by the following Formulas XIII, XIV, XV or XVI

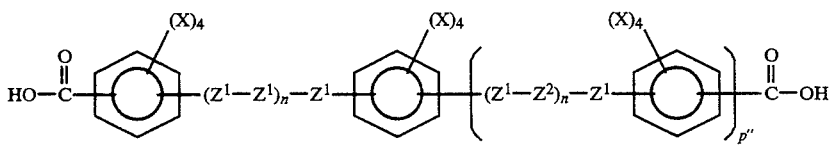

Formula XIII

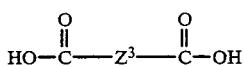

Formula XIV

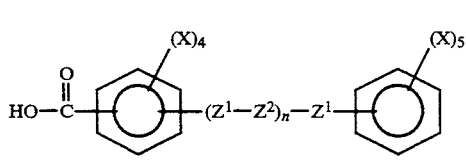

Formula XV

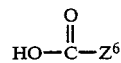

Formula XVI wherein at least about 80 percent of the $-(Z^1-Z^2)_n-Z^1-$ linkages and the carboxylic acid groups are in the para position with respect to each other; wherein $R^1$, X, $X^1$ $Z^1$, $Z^2$, $Z^3$, $Z^4$, $Z^6$, n, n' and p'' are as previously defined.

Particularly suitable carboxylic acid containing compounds include, for example, 4,4'-dicarboxy-α-methylstilbene, 4,4'-dicarboxybenzanilide, 4,4'-dicarboxy-2,2'-dimethylazoxybenzene, 4,4'-dicarboxystilbene, 4,4'-dicarboxyazobenzene, 4,4'-dicarboxyazoxybenzene, 4,4'-dicarboxy-α-cyanostilbene, 4,4'-dicarboxydiphenylacetylene, N,N'-bis(4-carboxyphenyl)terephthalamide, 4,4'-dicarboxy-3,3',5,5'-tetramethylstilbene, 4,4'-dicarboxy-3,3',5,5'-tetrabromostilbene, 4,4'-dicarboxy-3,3',5,5'-tetramethyl-α-methylstilbene, N-biphenyl-4-carboxybenzamide, N-2-naphthyl-4-carboxybenzamide, N-phenyl-4-carboxybenzamide, N-(4'-carboxyphenyl)-benzamide, 4-carboxystilbene, 4-carboxy-α-methylstilbene, 4-carboxyazobenzene, 4-carboxy-α-cyanostilbene, 4-carboxyazoxybenzene, 4,4'-dicarboxydiphenylazomethine, any combination thereof and the like.

Suitable catalysts which can be employed to prepare the mono and polyglycidyl esters of the present invention include, for example, ammonium halides such as, for example, benzyltrimethylammonium chloride, benzyltrimethylammonium bromide, tetrabutylammonium chloride, tetrabutylammonium bromide, tetraoctylammonium chloride, tetraoctylammonium bromide, tetramethylammonium chloride, tetramethylammonium bromide, any combination thereof and the like.

Suitable basic acting compounds which can be employed to prepare the mono and polyglycidyl esters of the present invention include, for example, alkali metal or alkaline earth metal hydroxides, carbonates, bicarbonates and the like. Particularly suitable such compounds include, for example, sodium hydroxide, potassium hydroxide, lithium hydroxide, calcium hydroxide, barium hydroxide, magnesium hydroxide, manganese hydroxide, sodium carbonate, potassium carbonate, lithium carbonate, calcium carbonate, barium carbonate, magnesium carbonate, manganese carbonate, sodium bicarbonate, potassium bicarbonate, lithium bicarbonate, calcium bicarbonate, barium bicarbonate, magnesium bicarbonate, manganese bicarbonate, mixtures thereof and the like. Most preferred is sodium hydroxide or potassium hydroxide.

Suitable solvents which can be employed herein include, for example, alcohols, aliphatic hydrocarbons, aromatic hydrocarbons, glycol ethers, amides, sulfoxides, sulfones, any combination thereof and the like. Particularly suitable solvents include, for example, methanol, ethanol, isopropanol, hexane, heptane, octane, nonane, decane, toluene, xylene, ethylene glycol methyl ether, ethylene glycol ethyl ether, ethylene glycol n-butyl ether, ethylene glycol phenyl ether, propylene glycol methyl ether, propylene glycol phenyl ether, tripropyiene glycol methyl ether, diethylene glycol methyl ether, diethylene glycol ethyl ether, diethylene glycol n-butyl ether, diethylene glycol phenyl ether, butylene glycol methyl ether, N,N-dimethylformamide, N-methylpyrrolidinone, N,N-dimethylacetamide, dimethylsulfoxide, sulfolane, any combination thereof and the like.

The solvent, if used, is usually employed in amounts suitably from about 5 to about 95, more suitably from about 20 to about 60, most suitably from about 30 to about 40, percent by weight based upon the combined weight of solvent and epihalohydrin.

Suitable compounds having an average of more than one active hydrogen atom per molecule which can be employed to prepare the advanced resin compositions of the present invention include, for example, basphenols, thiobisphenols, dicarboxylic acids and compounds containing one primary amine or amide group or two secondary amine groups such as those represented by the following Formulas XVII or XVIII;

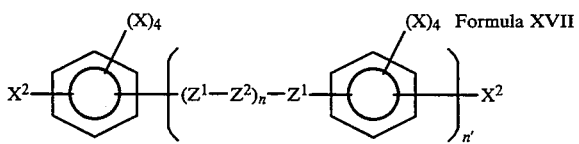

Formula XVII

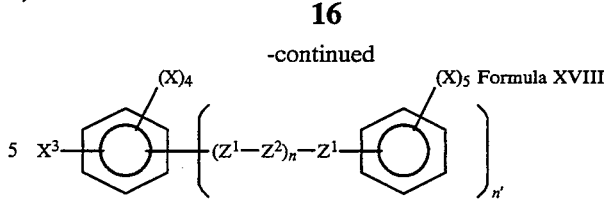

Formula XVIII wherein $X^2$ is independently a hydroxyl, carboxylic acid, —SH, or —NHR$^2$ group; R$^2$ is an alkyl group having from 1 to about 4 carbon atoms; $X^3$ is —NH$_2$, NH$_2$—SO$_2$—, NH$_2$—CO—, or NH$_2$—Z$^5$—O—; Z$^5$ is an alkylidene or cycloalkylidene group having from 1 to about 12 carbon atoms; and wherein Z$^1$, X, Z', R$^1$, Z$^2$, n and n' are as hereinbefore defined.

The advancement of the polyglycidyl esters containing one or more mesogenic moieties with compounds having an average of more than one active hydrogen per molecule is employed to linearly chain extend the resin. This linear chain extension is required for some mesogen-containing resin compositions in order to obtain liquid crystal character. The advancement of the mesogenic polyglycidyl ester resins can also be used to increase the temperature range in which a particular resin is liquid crystalline and to control the degree of crosslinking during the final curing stage.

The polyglycidyl ester containing one or more mesogenic moieties and the compound having an average of more than one active hydrogen atom per molecule are reacted in amounts which provide suitably from about 0.01:1 to about 0.95:1, more suitably from about 0.05:1 to about 0.9:1, most suitably from about 0.10:1 to about 0.50:1 active hydrogen atoms per epoxy group.

Particularly suitable compounds having an average of more than one active hydrogen atom per molecule which can be employed herein include hydroxyl-containing compounds, carboxylic acid-containing compounds and primary amine-containing compounds. These compounds include, for example, those represented by Formulas XVII and XVIII.

Particularly suitable hydroxyl-containing compounds include, for example, hydroquinone, bisphenol A, 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachorobisphenol A, 3,3'-dimethoxybisphenol A, 4,4'-dihydroxybiphenyl, 4,4'-dihydroxy-α,α'-diethylstilbene, 4,4'-dihydroxy-α-methylstilbene, 4,4'-dihydroxybenzanilide, 4,4'-dihydroxy-2,2'-dimethylazoxybenzene, 4,4'-dihydroxy-α-cyanostilbene, bis(4-hydroxyphenyl)terephthalate, N,N'-bis(4-hydroxyphenyl)terephthalamide, bis(4'-hydroxybiphenyl)terephthalate, 4,4'-dihydroxyphenylbenzoate, bis(4'- hydroxyphenyl)-1,4-benzenediimine, 4,4''-dihydroxybiphenylbenzoate, 1,4-bis(4'-hydroxyphenyl-1'-carboxamide)benzene, 1,4-bis(4'-hydroxyphenyl-1'-carboxy)benzene, 4,4'-bis(4''-hydroxyphenyl-1''-carboxy)-biphenyl, mixtures thereof and the like.

Particularly suitable carboxylic acid-containing compounds include, for example, terephthalic acid, 4,4'-benzanilide dicarboxylic acid, 4,4'-phenylbenzoate dicarboxylic acid, 4,4'-stilbene dicarboxylic acid, 4,4'-dicarboxybiphenyl, 4,4'-dicarboxychalcone, 4,4'-dicarboxydiphenylazomethine, and mixtures thereof and the like.

Particularly suitable primary amine-containing compounds include, for example, aniline, 4'-sulfonamido-N-phenyl benzamide, 4'-sulfonamido-N'-phenyl-4- chlorobenzamide, 4-amino-1-phenylbenzoate, 4-amino-N-phenylbenzamide, N-phenyl-4-amino-phenyl-1-carboxamide, phenyl-4-aminobenzoate, biphenyl-4-aminobenzoate, 1-phenyl-4'-aminophenylterephthalate, mixtures thereof and the like.

The advancement reaction can be conducted in the presence of a suitable advancement catalyst such as, for example, phosphines, quaternary ammonium compounds, phosphonium compounds, tertiary amines and the like. Particularly suitable catalysts include, for example, ethyltriphenylphosphonium chloride, ethyltriphenylphosphonium bromide, ethyltriphenylphosphonium iodide, ethyltriphenylphosphonium diacetate (ethyltriphenylphosphonium acetate.acetic acid complex), ethyltriphenylphosphonium phosphate, tetrabutylphosphonium chloride, tetrabutylphosphonium bromide, tetrabutylphosphonium iodide, tetrabutylphosphonium diacetate (tetrabutylphosphonium acetate.acetic acid complex), butyltriphenylphosphonium tetrabromobisphenate, butyltriphenylphosphonium bisphenate, butyltriphenylphosphonium bicarbonate, benzyltrimethylammonium chloride, tetramethylammonium hydroxide, triethylamine, tripropylamine, tributylamine, 2-methylimidazole, benzyldimethylamine, mixtures thereof and the like. Many of these catalysts are described in U.S. Pat. Nos. 3,306,872; 3,341,580; 3,379,684; 3,477,990; 3,547,881; 3,637,590; 3,843,605; 3,948,855; 3,956,237; 4,048,141; 4,093,650; 4,131,633; 4,132,706; 4,171,420; 4,177,216 and 4,366,295, all of which are incorporated herein by reference.

The amount of advancement catalyst depends, of course, upon the particular reactants and catalyst employed; however, it is usually employed in quantities of from about 0.03 to about 3, preferably from about 0.03 to about 1.5, most preferably from about 0.05 to about 1.5 percent by weight based upon the weight of the epoxy-containing compound.

The advancement reaction can be conducted at atmospheric, superatmospheric or subatmospheric pressures at temperatures of from about 20° C. to about 260° C., preferably from about 80° C. to about 240° C., more preferably from about 100° C. to about 200° C. The time required to complete the advancement reaction depends upon the temperature employed. Higher temperatures require shorter periods of time whereas lower temperatures require longer periods of time. Generally, however, times of from about 5 minutes to about 24 hours, preferably from about 30 minutes to about 8 hours, more preferably from about 30 minutes to about 3 hours are suitable.

If desired, the advancement reaction can be conducted in the presence of one or more solvents. Suitable such solvents include, for example, glycol ethers, aliphatic and aromatic hydrocarbons, aliphatic ethers, cyclic ethers, ketones, esters, amides, any combination thereof and the like. Particularly suitable solvents include, for example, toluene, benzene, xylene, methyl ethyl ketone, methyl isobutyl ketone, diethylene glycol methyl ether, dipropylene glycol methyl ether, dimethylformamide, dimethylsulfoxide, N-methylpyrrolidinone, tetrahydrofuran, propylene glycol methyl ether, any combination thereof and the like. The solvents can be employed in amounts of from about zero to about 80%, preferably from about 20% to about 60%, more preferably from about 30% to about 50% by weight based upon the weight of the reaction mixture.

When the polyglycidyl ester containing one or more mesogenic moieties and the compound having an average of more than one active hydrogen atom per molecule are reacted in amounts which provide from about 0.96:1 to about 1.05:1 active hydrogen atoms per epoxy group, a relatively high molecular weight substantially thermoplastic resinous product is produced. These essentially thermoplastic resin compositions contain little, if any, curable residual epoxide functionality and may even contain an active hydrogen functionality, depending upon which component is employed in excess, the polyglycidyl ester or the active hydrogen containing compound. These thermoplastic resinous compositions can thus be processed using the typical processing methods employed with conventional thermoplastic resins, such as, for example, injection molding or extrusion. Thermosetting may, however, be induced, for example, via reaction of all or a part of the backbone secondary aliphatic hydroxyl groups produced in the aforesaid advancement reaction, with a curing agent therefor. One class of suitable curing agents includes, for example, the di or polyisocyanates, as well as the blocked di or polyisocyanates which can be induced to react with the secondary hydroxyl groups providing urethane crosslinks between the resin chains. An example of a specific diisocyanate especially useful herein is 4,4'-diisocyanatodiphenylmethane. If desired, the reaction can be conducted in the presence of a suitable catalyst such as, for example, those catalysts described herein for use the advancement reaction.

The compositions of the present invention containing an average of more than one vicinal epoxy group per molecule can be cured with any suitable curing agent for curing epoxy-containing resins such as, for example, primary and secondary polyamines, carboxylic acids and anhydrides thereof, aromatic hydroxyl containing compounds, imidazoles, guanidines, urea-aldehyde resins, melamine-atdehydes resins, alkoxylated urea-aldehyde resins, alkoxylated melamine-aldehyde resins, aliphatic amines, cycloaliphatic amines, aromatic amines, any combination thereof and the like. The curing agents can contain one or more mesogenic moieties or they can be free of mesogenic moieties. Particularly suitable curing agents which are essentially free of mesogenic moieties include, for example, methylene dianiline, dicyandiamide, ethylene diamine, diethylenetriamine, triethylenetetramine, tetraethylenepentamine, urea-formaldehyde resins, melamine-formaldehyde resins, methylolated urea-formaldehyde resins, methylolated melamine-formaldehyde resins, phenol-formaldehyde novolac resins, cresol-formaldehyde novolac resins, sulfanilamide, diaminodiphenylsulfone, diethyltoluenediamine, t-butyltoluenediamine, bis-4-aminocyclohexylmethane, isophoronediamine, diaminocyclohexane, hexamethylenediamine, piperazine, aminoethylpiperazine, 2,5-dimethyt-2,5-hexanediamine, 1,12-dodecanediamine, tris-3-aminopropylamine, any combination thereof and the like.

Suitable curing agents which contain one or more mesogenic moieties include, for example, 4,4'-stilbenedicarboxylic acid, 4,4'-dicarboxychalcone, 4,4'-diaminobenzanilide, or any combination thereof and the like.

The curing agents are employed in amounts which will effectively cure the composition; however, these amounts will depend upon the particular polyglycidyl ester and curing agent employed. Generally, suitable amounts include, for example, from about 0.95:1 to about 1.2:1 equivalents of curing agent per equivalent of polyglycidyl ester.

The monoglycidyl esters containing one or more mesogenic moieties of the present invention can be employed as reactive diluents for the polyglycidyl esters of the present invention as well as for polyglycidyl esters substantially free of mesogenic moieties, or epoxy resins. For polyglycidyl esters free of mesogenic moieties, the monoglycidyl esters provide a means of incorporating mesogenic moieties into the composition so as to enhance one or more properties when cured.

The mesogenic polyglycidyl esters of the present invention can also be employed for the purpose of improving the properties of epoxy resins substantially free of mesogenic moieties. Generally, suitable amounts of mesogenic polyglycidyl esters are from about 1 to about 99, more suitably from about 10 to about 80, most suitably from about 10 to about 50 weight percent based on the total weight of the combined resins. Representative of the epoxy resins free of mesogenic moieties include, for example, the diglycidyl ethers of resorcinol, bisphenol A, 4,4'-dihydroxydiphenylmethane, 3,3',5,5'-tetrabromobisphenol A, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachlorobisphenol A, 3,3'-dimethoxybisphenol A; the triglycidyl ether of tris(hydroxyphenyl)methane; the polyglycidyl ether of a phenol or substituted phenol-aldehyde condensation product (novolac); the polyglycidyl ether of a dicyclopentadiene or an oligomer thereof and phenol condensation product; the advancement reaction products of the aforesaid di- and polyglycidyl ethers with aromatic di- or polyhydroxyl or carboxylic acid-containing compounds including, for example, bisphenol A (4,4'-isopropylidenediphenol), o-, m-, p-dihydroxybenzene, 2,4-dimethylresorcinol, 4-chlororesorcinol, tetramethylhydroquinone, 1,1-bis(4-hydroxyphenyl)ethane, 1,1-bis(4-hydroxyphenyl)-1-phenylethane, 4,4'-dihydroxydiphenyl ether, 3,3',5,5'-tetramethyldihydroxydiphenyl ether, 3,3',5,5'-dichlorodihydroxydiphenyl ether, 4,4'-bis-(p-hydroxyphenyl isopropyl)diphenyl ether, 4,4'-bis-(p-hydroxyphenoxy)benzene, 4,4'-bis(p-hydroxyphenoxy)-diphenyl ether, 4,4'-bis(4(4-hydroxyphenoxy)phenyl sulfone)diphenyl ether, 4,4'-dihydroxydiphenyl sulfone, 4,4'-dihydroxydiphenyl sulfide, 4,4'-dihydroxydiphenyl disulfide, 2,2'-dihydroxydiphenyl sulfone, 4,4'-dihydroxydiphenyl methane, 1,1-bis(p-hydroxyphenyl)cyclohexane, 4,4'-dihydroxybenzophenone, phloroglucinol, pyrogallol, 2,2',5,5'-tetrahydroxydiphenyl sulfone, tris(hydroxyphenyl)methane, dicyclopentadiene diphenol, tricyclopentadiene diphenol; mixtures thereof and the like.

Before and/or during processing and/or curing of the polyglycidyl ester compositions into a part, electric or magnetic fields or shear stresses can be applied for the purpose of orienting the liquid crystal moieties contained or developed therein which in effect improves the mechanical properties. As specific examples of these methods, Finkelmann, et al, *Macromol. Chem.*, 180, 803–806 (March 1979) induced orientation in thermotropic methacrylate copolymers containing mesogenic side chain groups decoupled from the main chain via flexible spacers in an electric field. Orientation of mesogenic side chain groups decoupled from the polymer main chain via flexible spacers in a magnetic field has been demonstrated by Roth and Kruecke, *Macromol. Chem.*, 187, 2655–2662 (November 1986). Magnetic field induced orientation of mesogenic main chain containing polymers has been demonstrated by Moore, et al, *ACS Polymeric Material Sciences and Engineering*, 52, 84–86 (April–May 1985). Magnetic and electric field orientation of low molecular weight mesogenic compounds is discussed by W. R. Krigbaum in *Polymer Liquid Crystals*, pages 275–309 (1982) published by Academic Press, Inc. All of the above are incorporated herein by reference in their entirety.

In addition to orientation by electric or magnetic fields, polymeric mesophases can be oriented by shear forces which are induced by drawing and/or flow through dies, orifices, and mold gates. A general discussion for orientation of thermotropic liquid crystal polymers by this method is given by S. K. Garg and S. Kenig in *High Modulus Polymers*, pages 71–103 (1988) published by Marcel Dekker, Inc. For the mesomorphic systems based on the polyglycidyl ester compositions, this shear orientation can be produced by processing methods such as injection molding, extrusion, pultrusion, filament winding, filming and preparing.

The mesogenic polyglycidyl esters of the present invention can be blended with other materials such as solvents or diluents, fillers, pigments, dyes, flow modifiers, thickeners, reinforcing agents, mold release agents, wetting agents, stabilizers, fire retardant agents, surfactants, any combination thereof and the like.

These additives are added in functionally equivalent amounts, e.g., the pigments and/or dyes are added in quantities which will provide the composition with the desired color; however, they are suitably employed in amounts of from about zero to about 20, more suitably from about 0.5 to about 5, most suitably from about 0.5 to about 3 percent by weight based upon the weight of the total blended composition.

Solvents or diluents which can be employed herein include, for example, hydrocarbons, ketones, glycol ethers, aliphatic ethers, cyclic ethers, esters, amides, any combination thereof and the like. Particularly suitable solvents or diluents include, for example, toluene, benzene, xylene, methyl ethyl ketone, methyl isobutyl ketone, diethylene glycol methyl ether, dipropylene glycol methyl ether, dimethylformamide, N-methylpyrrolidinone, tetrahydrofuran, propylene glycol methyl ether, any combination thereof and the like.

The modifiers such as thickeners, flow modifiers and the like can be suitably employed in amounts of from zero to about 10, more suitable from about 0.5 to about 6, most suitably from about 0.5 to about 4 percent by weight based upon the weight of the total composition.

Reinforcing materials which can be employed herein include natural and synthetic fibers in the form of woven fabric, mats, monofilament, multifilament, unidirectional fibers, rovings, random fibers or filaments, inorganic fillers or whiskers, hollow spheres, and the like. Suitable reinforcing materials include, glass, ceramics, nylon, rayon, cotton, aramid, graphite, polyalkylene terephthalates, polyethylene, polypropylene, polyesters, any combination thereof and the like.

Suitable fillers which can be employed herein include, for example, inorganic oxides, ceramic microspheres, plastic microspheres, glass microspheres, inorganic whiskers, $CaCO_3$, any combination thereof and the like.

The fillers can be employed in amounts suitable from about zero to about 95, more suitably from about 10 to about 80, most suitably from about 40 to about 60 percent by weight based upon the weight of the total composition.

The polyglycidyl esters of the present invention and advanced polyglycidyl esters of the present invention are useful in coating, laminate, composite, encapsulation, molding, casting, adhesive, sealant, foam, fiber and the like applications.

The monoglycidyl esters of the present invention are useful as reactive diluents for compounds containing an average of more than one glycidyl group per molecule. Those monoglycidyl esters which contain a polymerizable ethylenically unsaturated group are useful in the preparations of polymers and copolymers with other monomer(s) containing a polymerizable ethylenically unsaturated group.

The following examples are illustrative of the present invention, but are not to be construed as to limiting its scope in any manner.

EXAMPLE 1

A. Synthesis of 4,4',α,β-Tetrabromodiphenylethane

α,β-Diphenylethane (60.0 grams, 0.329 mole) and acetic acid (660 milliliters) are added to a one liter glass resin kettle reactor and stirred at 22° C. to provide a solution. A mixture of bromine (82 milliliters) and deionized water (32 milliliters) is added to the solution in the reactor and heating commences. After twenty five minutes, a reflux is achieved at a 103° C. temperature. At this time, crystalline white product is observed suspended in the reactor. After 45 minutes, the reflux temperature has reached 108° C. and extensive white crystalline product is observed suspended in the reactor. The product is recovered by filtration through a coarse fritted glass funnel, washed with acetic acid (200 milliliters) then washed with diethylether (50 milliliters). After drying in a vacuum oven at 60° C., a constant weight of 56.98 grams of white crystalline powder is obtained.

B. Synthesis of 4,4'-Dicyanostilbene 4,4',α,β-Tetrabromodiphenylethane from A above (56.90 grams, 0.114 mole), cuprous cyanide (63.73 grams, 0.712 mole) and pyridine (64.0 milliliters) are added to a one liter glass resin kettle reactor and stirred as a powder with heating. Once the temperature reaches 148° C., a black solution formed. After an additional thirty minutes, the reaction temperature reaches 205° C. and is held therein for an additional eighty three minutes. After this time, additional pyridine (136.6 milliliters) is added to the reactor and causes the temperature to decrease to 132° C. This temperature is maintained for five minutes, then the product is poured into a beaker containing stirred concentrated hydrochloric acid (341.4 milliliters) over a twelve minute period. The resultant black slurry is filtered while at 87° C. to provide a black powder product which is washed with additional concentrated hydrochloric acid (113.8 milliliters), then with deionized water (100 milliliters). The gray brown powder product is recovered then dried in a forced air oven at 100° C. to a constant weight of 37.12 grams. Recrystallization is completed by boiling the crude product in nitrobenzene (175 milliliters) followed by filtration through a coarse fritted glass funnel to remove a black insoluble residue. The filtrate is stored at 4° C. for twelve hours then the crystalline product is recovered by filtration. After drying at ambient temperature (23° C. to 25° C.) for 48 hours, 14.3 grams (slight odor of nitrobenzene still present) of shimmering light brown needles of 4,4'-dicyanostilbene are obtained.

C. Synthesis of Diiminoethylether dihydrochloride of 4,4'-Dicyanostilbene 4,4'-Dicyanostilbene from B above (14.3 grams), and nitrobenzene (572 milliliters) are combined in a beaker and brought to a boil (208° C.) with stirring. The resultant solution is added to a one liter glass resin kettle reactor and stirred with cooling. After twelve minutes, the temperature reaches 25° C., and anhydrous ethanol (35.8 milliliters) is added to the reactor. After an additional ten minutes, the reaction temperature reaches 0° C. and sparging with anhydrous hydrogen chloride commences. Two minutes after beginning the sparge, the temperature exotherms to 9° C. while maintaining the cooling bath on the reactor at −52° C. After an additional nine minutes, the temperature decreases to −1° C. and sparging is terminated. After an additional seven minutes, the temperature decreases to −2° C. and the cooling bath is removed from the reactor and the contents therein allowed to warm to room temperature (24° C.). After 48 hours, the reactor contents are filtered through a coarse fritted glass funnel. The light yellow powder retained on the funnel is washed with anhydrous diethylether (75 milliliters) to provide 31.56 grams (slightly wet) diiminoethylether dihydrochloride product.

D. Synthesis of Diethyl-4,4'-stilbenedicarboxylate

Diiminoethylether dihydrochloride of 4,4'-dicyanostilbene from C above (31.56 grams, slightly wet) and deionized water (95 milliliters) are added to a one liter glass resin kettle reactor and stirred with heating. After twenty five minutes, the temperature reaches 100° C. and is held therein for one hour. The product is recovered by filtration on paper as a light tan colored powder then dried at ambient temperature (24° C.) for twelve hours to provide 19.4 grams (slightly wet) diethyl-4,4'-stilbenedicarboxylate.

E. Hydrolysis of Diethyl-4,4'-stilbenedicarboxylate

Diethyl-4,4'-stilbenedicarboxylate from D above (19.4 grams, slightly wet), ethylene glycol (323 grams), deionized water (81 grams) and sodium hydroxide (40.4 grams) are added to a resin kettle reactor and stirred with heating. After nineteen minutes, a reflux is achieved at 126° C. and is held therein for six hours. The reaction product is diluted into deionized water (3 liters) and the resultant solution passed through a filter. The filtrate is added to a beaker, stirred and acidified to a pH of one with concentrated hydrochloric acid. The resultant gelatinous white slurry is heated to 80° C. then filtered through paper to recover a white powder product. After washing with deionized water (100 milliliters), the product is dried in a forced air oven at 80° C. for fourteen hours to a constant weight of 14.4 grams. Fourier transform infrared spectrophotometric analysis of a potassium chloride pellet confirmed the product structure for 4,4'-stilbenedicarboxylic acid.

F. Epoxidation of 4,4'-Stilbenedicarboxylic Acid 4,4'-Stilbenedicarboxylic acid (13.41 grams, 0.10 —COOH equivalent) from E above, epichlorohydrin (231.33 grams, 2.5 mole) and tetrabutylammonium chloride (0.134 gram, 1.0% wt. of the diacid reactant used) are added to a one liter glass round bottom reactor and heated to 60° C. with magnetically driven stirring under a nitrogen atmosphere flowing at a rate of one liter per minute. After twenty hours at the 60° C. reaction temperature, Fourier transform infrared spectrophotometric analysis demonstrates incomplete conversion of the carboxylic acid groups (acid carbonyl absorbance at 1682 cm$^{-1}$) to ester groups (ester carbonyl absorbance at 1716 cm$^{-1}$) hence the reaction temperature is increased to 80° C. After 156 minutes at the 80° C. reaction temperature, Fourier transform infrared spectrophotometric analysis demonstrates complete conversion of the carboxylic acid groups to ester groups concurrent with the formation of a hazy, light brown colored solution. At this time, a water separator is interspersed between the reactor and the chilled (−2.5° C.) glycol condenser and an addition funnel containing sodium hydroxide (4.5 grams, 0.113 mole) dissolved in deionized water (5.5 grams, 55% wt. of the solution) and a vacuum line are added to the reactor. The nitrogen purge is shut off simultaneous with initiation of the vacuum. The vacuum and reaction temperature are equilibrated at 84 mm Hg and 60° C., respectively and such that a vigorous reflux is maintained with continuous return of dry epichlorohydrin from the water separator to the reactor. After equilibration, dropwise addition of the aqueous sodium hydroxide commences accompanied by a gradual reduction in vacuum and reaction temperature. After 42 minutes, addition of the aqueous sodium hydroxide is complete and vacuum and reaction temperature are at 65 mm Hg and 55° C., respectively. After an additional 2 hours at the 65 mm Hg vacuum and 55° C. reaction temperature, heating ceases and the product slurry is cooled to 50° C. The recovered slurry is filtered under a nitrogen atmosphere and the resultant light amber colored solution rotary evaporated under a vacuum (5 mm Hg final conditions) at 90° C. for 30 minutes. The product is recovered (14.0 grams) as a white powder. Titration of a portion of the product reveals an epoxide equivalent weight of 192.81. Fourier transform infrared spectrophotometric analysis of a potassium chloride pellet of the product confirms the product structure for the diglycidyl ester of 4,4'-stilbenedicarboxylic acid (ester carbonyl absorbance at 1716 cm$^{-1}$, epoxide C—O stretching absorbance at 852 and 906 cm$^{-1}$).

G. Characterization of Liquid Crystallinity in the Diglycidyl Ester of 4,4'-Stilbenedicarboxylic Acid Analysis of the diglycidyl ester of 4,4'-stilbenedicarboxylic acid from F above via crosspolarized light microscopy is completed using an optical microscope equipped with a programmable hot stage using a heating rate of 10° C. per minute. The results are reported in Table I.

TABLE I

CROSSPOLARIZED LIGHT MICROSCOPY ANALYSIS OF THE DIGLYCIDYL ESTER OF 4,4'-STILBENEDICARBOXYLIC ACID

| Cycle Designation | Observed Transition Temperatures (°C.) | Comments |
| --- | --- | --- |
| First heating | 30[1] | [1]Birefringent crystalliine solid. |
|  | 129[2] | [2]First fluidity noted. |
|  | 135[3] | [3]Isotropization completed |
| First cooling | 106[1] | [1]First mobile nematic texture formed. |
|  | 92[2] | [2]First crystallization noted. |
| Second heating | 30[1] | [1]Birefringent crystalline solid. |
|  | 132[2] | [2]Isotropization completed. |

TABLE I-continued

CROSSPOLARIZED LIGHT MICROSCOPY ANALYSIS OF THE DIGLYCIDYL ESTER OF 4,4'-STILBENEDICARBOXYLIC ACID

| Cycle Designation | Observed Transition Temperatures (°C.) | Comments |
| --- | --- | --- |
| Second cooling | 106[1] | [1]First mobile nematic texture formed. |
|  | 88[2] | [2]First crystallization noted. |

The diglycidyl ester is a monotropic liquid crystal with a nematic texture.

Analysis of a portion (12.5 milligrams) of the diglycidyl ester of 4,4'-stilbenedicarboxylic acid from F above via differential scanning calorimetry is completed using a heating and cooling rate of 5° C. per minute under nitrogen flowing at 35 cubic centimeters per minute over a temperature range of 35° C. to 160° C. The results are reported in Table II.

TABLE II

DIFFERENTIAL SCANNING CALORIMETRY ANALYSIS OF THE DIGLYCIDYL ESTER OF 4,4'-STILBENEDIICARBOXYLIC ACID

| Cycle Designation | Observed Transition Temperatures (°C.) peak/range | Enthalpy (J/G) | Comments |
| --- | --- | --- | --- |
| First heating | 131/105 to 140 | 77.8 | Endotherm |
| First cooling | 104/107 to 100 | 0.74 | Exotherm |
|  | 92/95 to 88 | 0.70 | Exotherm |
|  | 69/80 to 55 | 31.3 | Exotherm |
| Second Heating | 128/110 to 135 | 51.7 | Endotherm |
| Second cooling | 105/108 to 100 | 0.81 | Exotherm |
|  | 90/92 to 87 | 0.44 | Exotherm |

H. Preparation of a Cured Casting of the Diglycidyl Ester of 4,4'-Stilbenedicarboxylic Acid and Evaluation of Susceptibility to Shear Induced Orientation During Cure A portion (0.5155 gram, 0.00268 epoxide equivalent) of the diglycidyl ester of 4,4'-stilbenedicarboxylic acid from F above and sulfanilamide (0.1152 gram, 0.00268 amine equivalent) is combined and ground together to form a homogeneous powder mixture. Differential scanning calorimetry analysis of a portion (8.2 milligrams) of the powder heated at 10° C. per minute under nitrogen flowing at 35 cubic centimeters per minute reveals an exotherm (195 joules per gram) between 125° and 225° C. A portion of the powder is placed between two glass plates and heated at 20° C. per minute to 125° C. at which point an isotropic melt is observed via optical microscopy (70× magnification) under crosspolarlzed light. Following formation of the isotropic melt, the resin is cooled to 120° C. A nematic liquid crystalline morphology and stir opalescence are produced by holding the resin at the 120° C. temperature for 20 minutes. After a total of 23 minutes at 120° C., shear is applied to the resin by moving the glass coverslip across the top of the resin. As a result of the application of shear, uniaxial orientation of the liquid crystal domains is visually observable in the direction that shear is applied. After one hour at 120° C., the resin is heated at 10° C. per minute to 250° C. At 250° C., the shear oriented morphology produced at 120° C. is observed to be maintained. A second portion of the powder is placed between two glass plates and heated directly to 140° C. After one minute, the isotropic melt produced is cooled at 10° C. per minute. On cooling, a nematic liquid crystalline morphology is observed at 84° C. Shear is applied at this temperature to the resin by moving the glass coverslip across the top of the resin. As a result of the application of shear at this temperature and degree of cure, uniaxial orientation of the liquid crystal domains is visually observable in the direction perpendicular to the direction that shear is applied. Following further cooling to 70° C. the resin viscosity is increased and shear is again applied to the resin. As a result of the application of shear, uniaxial orientation of the liquid crystalline domains is visually observable in the direction that shear is applied. For the preparation of a cured casting, the remaining powder is transferred to an aluminum cup. The aluminum cup is placed in an oven which has been preheated to 140° C. and the powder is observed to melt to a translucent liquid. After 5 minutes at 140° C., the oven temperature is reduced to 120° C. and maintained therein for 3 hours before increasing the temperature 20° C. per hour to a final temperature of 200° C. After four hours at 200° C., an opaque casting is recovered from the aluminum cup. This casting exhibits a high level of birefringence when viewed by optical microscopy (70× magnification) under crosspolarized light. Differential scanning calorimetry of a portion of the casting using the aforementioned conditions reveals a glass transition temperature of 190° C.

EXAMPLE 2

Preparation of a Cured Composition of the Diglycidyl Ester of 4,4'-Stilbenedicarboxylic Acid and 4,4'-Stilbenedicarboxylic Acid A portion (0.3338 gram, 0.00173 epoxide equivalent) of the diglycidyl ester of 4,4'-stilbenedicarboxylic acid from Example 1-F and a portion (0.2324 gram, 0.00173 —COOH equivalent) of 4,4'-stilbenedicarboxylic acid from Example 1-E are dissolved in acetone (30 milliliters) containing tetrabutylphosphonium acetate.acetic acid complex (0.0012 gram, 0.36 phr based on the glycidyl ester reactant used). After mixing the solution for one hour, a homogeneous powder mixture is recovered by evaporation of the acetone solvent. Differential scanning calorimetry analysis of a portion (10.2 milligrams) of the powder heated at 10° C. per minute under nitrogen flowing at 35 cubic centimeters per minute reveals an exotherm (199 joules per gram) between 130° and 250° C. A portion of the powder is placed between two glass plates and heated directly to 160° C. at which point an opaque melt containing dispersed birefringent domains is observed via optical microscopy (70× magnification) under crosspolarized light. Following formation of the opaque melt, the resin solidified within 90 seconds to an opaque, birefringent solid. For the preparation of a cured casting, the remaining powder is transferred to an aluminum cup. The aluminum cup is placed in an oven which has been preheated to 160° C. After one hour at 160° C., the oven temperature is increased 30° C. per hour to a final temperature of 230° C. After six hours at 230° C., an opaque casting is recovered from the aluminum cup. This casting exhibits a crystalline appearance when viewed by optical microscopy (70× magnification) under crosspolarized light. Differential scanning calorimetry of a portion of the casting using the aforementioned conditions reveals a glass transition temperature of 246° C.

EXAMPLE 3

A. Synthesis of 4,4'-Dicarboxychalcone

4-Carboxyacetophenone (19.70 grams, 0.12 mole), 4-carboxybenzaldehyde (18.02 grams, 0.12 mole) and absolute ethanol (500 milliliters) are added to a one liter glass resin kettle reactor and stirred as a slurry under a nitrogen flowing at one liter per minute. The slurry is cooled to 5° C. using an external cooling bath, then sparging with anhydrous hydrogen chloride commences and induced a maximum exotherm to 26° C. one minute later. At this time, sparging is stopped and cooling back to 5° C. completed over the next two minutes. Once the 5° C. temperature is reachieved, sparging with hydrogen chloride resumes and induces a maximum exotherm to 7° C. Sparging continues until cooling reestablishes the 5° C. reaction temperature and is then terminated. The thick light yellow colored, stirred slurry is allowed to warm to room temperature (24° C.) over a fifteen hour period. The crude product is recovered by filtration and washed with deionized water until the wash water possesses a neutral pH. After drying in a vacuum oven at 65° C., a constant weight of 31.2 grams of a crystalline, light yellow colored powder is obtained. Nuclear magnetic resonance spectroscopy and Fourier transform infrared spectrophotometric analysis of a potassium chloride pellet of the product demonstrates the presence of a minor amount of the aldol in addition to the desired 4,4-dicarboxychalcone.

Dehydration of the residual aldol is completed via addition of a portion (19.23 grams) of the crystalline, light yellow colored powder to phosphoric acid (85 percent) (400 grams) in a one liter glass round bottom reactor. Stirring and heating commences until the slurry reaches a temperature of 150° C. After one hour at 150° C., additional phosphoric acid (200 grams) is added to the stirred slurry with cooling to 100° C. After 12 hours at the 100° C. temperature, the slurry is diluted with deionized water (1000 milliliters), filtered through paper, and the resultant product washed with deionized water until the wash water possesses a neutral pH. After drying in a vacuum oven at 100° C., a constant weight of 17.08 grams of crystalline, light yellow colored powder is obtained. Nuclear magnetic resonance spectroscopy and Fourier transform infrared spectrophotometric analysis of a potassium chloride pellet of the product confirms the product structure of dicarboxychalcone (ketone carbonyl absorbance at 1663 cm$^{-1}$, carboxylic acid carbonyl absorbance at 1689 cm$^{-1}$, carboxylic acid O—H stretching absorbances at 2993, 2884, 2825, 2671 and 2546 cm$^{-1}$). Differential scanning calorimetry of a portion (11.40 milligrams) of the product heated at 10° C. per minute under nitrogen flowing at 35 cubic centimeters per minute revealed a sharp melting point endotherm at 369.3° C. which is immediately followed by exothermic decomposition.

B. Epoxidation of 4,4'-Dicarboxychalcone 4,4'-Dicarboxychalcone (14.81 grams, 0.10 —COOH equivalent) from A above, epichlorohydrin (231.33 grams, 2.5 mole) and tetrabutylammonium chloride (0.148 gram, 1.0% wt. of the diacid reactant used) are added to a one liter glass round bottom reactor and heated to 60° C. with magnetically driven stirring under a nitrogen atmosphere flowing at a rate of one liter per minute. After sixteen hours at the 60° C. reaction temperature, Fourier transform infrared spectrophotometric analysis demonstrates incomplete conversion of the carboxylic acid groups (acid carbonyl absorbance at 1689 cm$^{-1}$) to ester groups (ester carbonyl absorbance at 1716 cm$^{-1}$) hence the reaction temperature is increased to 80° C. After 167 minutes at the 80° C. reaction temperature, Fourier transform infrared spectrophotometric analysis demonstrates complete conversion of the carboxylic acid groups to ester groups concurrent with the formation of a hazy, light brown colored solution. At this time, a water separator is interspersed between the reactor and the chilled (−2.5° C.) glycol condenser and an addition funnel containing sodium hydroxide (4.5 grams, 0.113 mole) dissolved in deionized water (5.5 grams, 55% wt. of the solution) and a vacuum line are added to the reactor. The nitrogen purge is shut off simultaneous with initiation of the vacuum. The vacuum and reaction temperature are equilibrated at 84 mm Hg and 60° C., respectively and such that a vigorous reflux is maintained with continuous return of dry epichlorohydrin from the water separator to the reactor. After equilibration, dropwise addition of the aqueous sodium hydroxide commences accompanied by a gradual reduction in vacuum and reaction temperature. After 71 minutes, addition of the aqueous sodium hydroxide is complete and vacuum and reaction temperature are at 65 mm Hg and 55° C., respectively. After an additional 3 hours at the 65 mm Hg vacuum and 55° C. reaction temperature, heating ceased and the product slurry is cooled to 50° C. The recovered slurry is filtered under a nitrogen atmosphere and the resultant light amber colored solution rotary evaporated under a vacuum (1 mm Hg final conditions) at 90° C. for 30 minutes. The product is recovered as a powder. The powder product is dissolved in methylene chloride (100 milliliters), then washed with deionized water (25 milliliters). The recovered methylene chloride layer is dried over anhydrous sodium sulfate, filtered, then the resultant filtrate rotary evaporated under vacuum to a constant weight of 19.19 grams of light tan colored powder. Titration of a portion of the product reveals an epoxide equivalent weight of 218.46. Fourier transform infrared spectrophotometric analysis of a potassium chloride pellet of the product confirms the product structure for the diglycidyl ester of 4,4'-dicarboxychalcone (ester carbonyl absorbance at 1722 cm$^{-1}$, ketone carbonyl absorbance at 1666 cm$^{-1}$, epoxide C—O stretching absorbance at 843 (853 slight shoulder) and 906 cm$^{-1}$).

C. Characterization of Liquid Crystallinity in the Diglycidyl Ester of 4,4'-Dicarboxychalcone Analysis of the diglycidyl ester of 4,4'-dicarboxychalcone from B above via crosspolarized light microscopy is completed using an optical microscope equipped with a programmable hot stage using a heating rate of 10° C. per minute. The results are reported in Table III.

TABLE III

CROSSPOLARIZED LIGHT MICROSCOPY ANALYSIS OF THE DIGLYCIDYL ESTER OF 4,4'-DICARBOXYCHALCONE

| Cycle Designation | Observed Transition Temperatures (°C.) | Comments |
| --- | --- | --- |
| First heating | 30[1] | [1]Birefringent crystalline solid. |
|  | 95[2] | [2]First fluidity noted. |
|  | 106[3] | [3]Isotropization completed |
| First cooling | 71[1] | [1]First crystallization |

TABLE III-continued

CROSSPOLARIZED LIGHT MICROSCOPY ANALYSIS OF THE DIGLYCIDYL ESTER OF 4,4'-DICARBOXYCHALCONE

| Cycle Designation | Observed Transition Temperatures (°C.) | Comments |
| --- | --- | --- |
|  | 30[2] | formed. [2]Birefringent semi-crystalline solid. |
| Second heating | 30[1] | [1]Birefringent semi-crystalline solid. |
|  | 106[2] | [2]Isotropization completed. |
| Second cooling | 74[1] | [1]First crystallization noted. |
|  | 30[2] | [2]Birefringement semi-crystalline solid. |

EXAMPLE 4

Preparation of a Cured Composition of the Dialycidyl Ester of 4,4'-Dicarboxychalcone and 4,4'-Dicarboxychalcone A portion (2.5102 grams, 0.01149 epoxide equivalent) of the diglycidyl ester of 4,4'-dicarboxychalcone from Example 3-B and a portion (1.7024 gram, 0.01149 —COOH equivalent) of 4,4'-dicarboxychalcone from Example 3-A are dissolved in acetone (50 milliliters) containing tetrabutylphosphonium acetate.acetic acid complex (0.0088 gram, 0.35 phr based on the glycidyl ester reactant used). After mixing the solution for thirty minutes, a homogeneous powder mixture is recovered by evaporation of the acetone solvent. Differential scanning calorimetry analysis of a portion (11.4 milligrams) of the powder heated at 10° C. per minute under nitrogen flowing at 35 cubic centimeters per minute reveals an exotherm between 110° C. and 260° C. For the preparation of a cured casting, a portion (3.5 grams) of the powder is transferred to a 1 inch by 1 inch by 0.125 inch stainless steel mold. The mold is placed in a mechanical press which has been preheated to 140° C. Once in the press, pressure is slowly applied over a seven minute period until 10,000 psi is achieved. After two hours at 140° C. and 10,000 psi, the press temperature is increased 180° C. where it is maintained for four hours before cooling to room temperature (24° C.). At room temperature, an opaque casting is recovered from the mold and is postcured for four hours at 230° C., then four hours at 260° C. The postcured casting exhibits a high level of birefringence when viewed by optical microscopy (70× magnification) under crosspolarized light. Differential scanning calorimetry of a portion of the casting using the aforementioned conditions reveals a glass transition temperature of 218° C.

EXAMPLE 5

A. Synthesis of 4,4'-Dicarboxydiphenylazomethine

4-Aminobenzoic acid (20.57 grams, 0.15 mole), 4-carboxybenzaldehyde (22.52 grams, 0.15 mole) and tetrahydrofuran (600 milliliters) are added to a one liter glass resin kettle reactor and stirred under a nitrogen atmosphere flowing at one liter per minute with heating. Once the temperature reaches 50° C. it is held therein for the next five hours. After this time, the solution is recovered and rotary evaporated under a vacuum at 50° C. until a total volume of 300 milliliters is reached. The recovered solution is cooled to room temperature (24° C.) the mixed with methylene chloride (500 milliliters).

The precipitated crystalline product is recovered by filtration. After drying in a vacuum oven at 90° C. and 5 mm Hg, a constant weight 16.4 grams of a crystalline, brilliant yellow colored powder is obtained. Fourier transform initrated spectrophotometric analysis of a potassium chloride pellet of the product confirms the product structure of 4,4'-dicarboxydiphenylazomethine (azomethine C=N absorbance contained in a complex band of peaks with minima at 1570, 1589 and 1609 cm$^{-1}$, carboxylic acid carbonyl absorbance at 1689 cm$^{-1}$, carboxylic acid O—H stretching absorbances at 2991, 2884, 2818, 2672 and 2552 cm$^{-1}$). Differential scanning calorimetry of a portion (5.90 milligrams) of the product heated at 10° C. per minute under nitrogen flowing at 35 cubic centimeters per minute reveals a sharp melting point endotherm at 235.5° C. which is immediately followed by exothermic decomposition.

B. Epoxidation of 4,4'-Dicarboxydiphenylazomethine 4,4'-Dicarboxydiphenylazomethine (15.00 grams, 0.1114 —COOH equivalent from equivalent) from A above, epichlorohydrin (257.8 grams, 2.79 mole) and tetrabutylammonium chloride (0.15 gram, 1.0% wt. of the diacid reactant used) are added to a one liter glass round bottom reactor and heated to 60° C. with magnetically driven stirring under a nitrogen atmosphere flowing at a rate of one liter per minute. After seventeen hours at the 60° C. reaction temperature, Fourier transform infrared spectrophotometric analysis demonstrated incomplete conversion of the carboxylic acid groups (acid carbonyl absorbance at 1696 cm$^{-1}$) to ester groups (ester carbonyl absorbance at 1716 cm$^{-1}$) hence the reaction temperature is increased to 80° C. After 217 minutes at the 80° C. reaction temperature, Fourier transform infrared spectrophotometric analysis demonstrated complete conversion of the carboxylic acid groups to ester groups concurrent with the formation of a light yellow colored solution. At this time, a water separator is interspersed between the reactor and the chilled (−2.5° C.) glycol condenser and an addition funnel containing sodium hydroxide (5.01 grams, 0.1254 mole) dissolved in deionized water (6.13 grams, 55% wt. of the solution) and a vacuum line are added to the reactor. The nitrogen purge is shut off simultaneous with initiation of the vacuum. The vacuum and reaction temperature are equilibrated at 84 mm Hg and 60° C., respectively and such that a vigorous reflux is maintained with continuous return of dry epichlorohydrin from the water separator to the reactor. After equilibration, dropwise addition of the aqueous sodium hydroxide commenced accompanied by a gradual reduction in vacuum and reaction temperature. After 60 minutes, addition of the aqueous sodium hydroxide is complete and vacuum and reaction temperature are at 65 mm Hg and 55° C., respectively. After an additional 3 hours at the 65 mm Hg vacuum and 55° C. reaction temperature, heating ceases and the product slurry is cooled to 50° C. The recovered slurry is filtered under a nitrogen atmosphere and the resultant light amber colored solution rotary evaporated under a vacuum (1 mm Hg final conditions) at 105° C. for 45 minutes. The product is recovered as a powder. The powder product is dissolved in methylene chloride (100 milliliters), then washed with deionized water (25 milliliters). The recovered methylene chloride layer is dried over anhydrous sodium sulfate, filtered, then the resultant filtrate rotary evaporated under a vacuum to a constant weight of 20.84 grams of white powder. Titration of a portion of the product reveals an epoxide equivalent weight of 209.31 (corrected for background from the azomethine nitrogen). Fourier transform infrared spectrophotometric analysis of a potassium chloride pellet of the product confirms the product structure for the diglycidyl ester of 4,4'-dicarboxydiphenylazomethine (ester carbonyl absorbance at 1716 cm$^{-1}$, azomethine C=N absorbance contained in a complex band of peaks with minima at 1576, 1596, 1602 (slight shoulder) and 1629 cm$^{-1}$, epoxide C—O stretching at 852 and 905 cm$^{-1}$).

C. Characterization of Liquid Crystallinity in the Diglycidyl Ester of 4,4'-Dicarboxydiphenylazomethine Analysis of the diglycidyl ester of 4,4'-dicarboxydiphenylazomethine from B above via crosspolarized light microscopy is completed using a optical microscope equipped with an programmable hot stage using a heating rate of 10° C. per minute. The results are reported in Table IV.

TABLE IV

CROSSPOLARIZED LIGHT MICROSCOPY ANALYSIS OF THE DIGLYCIDYL ESTER OF 4,4'-DICARBOXYDIPHENYLAZOMETHINE

| Cycle Designation | Observed Transition Temperatures (°C.) | Comments |
|---|---|---|
| First heating | 30[1] | [1]Birefringent semi-solid. |
| | 40[2] | [2]First fluidity noted. |
| | 59[3] | [3]Isotropization completed. |
| First cooling | 50[1] | [1]First birefringent droplets observed. |
| | 44[2] | [2]Batonnets first observed. |
| | 40[3] | [3]First mobile mosaic texture observed. |
| | 23[4] | [4]First crystallization noted after 30 minutes. |
| Second heating | 30[1] | [1]Birefringent semi-solid. |
| | 82[2] | [2]Isotropization completed. |
| Second cooling | 54[1] | [1]First birefringent droplets observed. |
| | 30[2] | [2]First mobile mosaic texture observed. |
| | 23[3] | [3]First crystallization noted after 30 minutes. |

The diglycidyl ester is a monotropic liquid crystal with a smectic texture. Analysis of a portion (19.83 milligrams) of the diglycidyl ester of 4,4'-dicarboxydiphenylazomethine from B above via differential scanning calorimetry is completed using a heating and cooling rate of 10° C. per minute under nitrogen flowing at 35 cubic centimeters per minute over a temperature range of −50° C. to 125° C. The results are reported in Table V.

TABLE V

DIFFERENTIAL SCANNING CALORIMETRY ANALYSIS OF THE DIGLYCIDYL ESTER OF 4,4'-DICARBOXYDIPHENYLAZOMETHINE

| Cycle Designation | Observed Transition Temperatures (°C.) peak/range | Enthalpy (J/G) | Comments |
|---|---|---|---|
| First heating | −6.3/−11.6 to −0.9 | — | Baseline inflection |
| | 59/31 to 97 | 36.5 | Endotherm |
| First cooling | 41/52 to 28 | 3.2 | Exotherm |
| | 9/14 to −2 | 0.8 | Exotherm |
| Second heating | −5.6/−9.2 to −1.9 | — | Baseline inflection |
| | 10.3/7.0 to 13.5 | — | |
| | 46/29 to 52 | 0.7 | Baseline |

TABLE V-continued

DIFFERENTIAL SCANNING CALORIMETRY ANALYSIS OF THE DIGLYCIDYL ESTER OF 4,4'-DICARBOXYDIPHENYLAZOMETHINE

| Cycle Designation | Observed Transition Temperatures (°C.) peak/range | Enthalpy (J/G) | Comments |
| --- | --- | --- | --- |
| | 71/52 to 91 | 1.0 | inflection Endotherm Endotherm |
| Second cooling | 38/44 to 24 | 1.8 | Exotherm |
| | 8/11 to 0 | 0.5 | Exotherm |

EXAMPLE 6

Preparation of a Cured Composition of the Diglycidyl Ester of 4,4'-Dicarboxydiphenylazomethine and Sulfanilamide Sulfanilamide (0.1456 gram, 0.0034 amine equivalent) is added to a portion (0.6448 grams, 0.0031 epoxide equivalent) of the diglycidyl ester of 4,4'-dicarboxydiphenylazomethine from Example 5-B as a melt contained in an aluminum cup in an oven which has been preheated to 130° C. After 10 minutes, all of the sulfanilamide has dissolved, then the oven temperature is reduced to 100° C. Differential scanning calorimetry analysis of a portion (14.4 milligrams) of the resin mixture heated at 10° C. per minute under nitrogen flowing at 35 cubic centimeters per minute revealed an exotherm (332 joules per gram) between 117° and 254° C. For the preparation of a cured casting, the resin mixture is maintained at the 100° C. temperature for four hours before increasing the temperature 20° C. per hour to a final temperature of 160° C. After six hours at 160° C. a semi-translucent casting is recovered from the aluminum cup. The postcured casting exhibited a dispersed second phase when viewed by optical microscopy (70× magnification) under crosspolarized light. Differential scanning calorimetry of a portion of the casting using the aforementioned conditions reveals a glass transition temperature of 153° C. After postcuring this casting for twelve hours at 180° C., the glass transition is observed by differential scanning calorimetry to have increased to 209° C.

EXAMPLE 7

A. Synthesis of 4,4'-Dimethylbenzanilide p-Methylbenzoic acid (95.31 grams, 0.70 mole), sodium ethoxide catalyst (0.2144 gram, 0.225% wt. of the p-methylbenzoic acid used) and N,N'-dimethylacetamide (575 grams) are added to a reactor equipped with a reflux condenser and stirred under a nitrogen atmosphere at 35° C. to provide a solution. p-Methylphenyl isocyanate (97.87 grams, 0.735 mole) is added over a two minute period inducing an exotherm to 40° C. At this time, heating of the reactor commences and a 160° C. temperature is achieved 52 minutes later. After three hours at the 160° C. reaction temperature, the reactor is cooled to 30° C. the the contents poured into deionized water (3.50 liters). A precipitated white crystalline product is recovered by filtration of the aqueous slurry then dried in a vacuum oven at 80° C. and 5 mm Hg for fifteen hours. The dry product and methanol (700 milliliters) are stirred together with heating to provide a solution at 63° C. After cooling the methanol solution to 4° C. for fourteen hours, a white crystalline product is filtered off and dried at 70° C. and 5 mm Hg in a vacuum oven to a constant weight of 135.6 grams. Fourier transform infrared spectrophotometric analysis of a potassium chloride pellet of the product confirms the product structure of 4,4'-dimethylbenzanilide (amide carbonyl absorbance at 1649 cm$^{-1}$ and amide N—H stretching absorbance at 3349 and 3290 (shoulder) cm$^{-1}$.

B. Synthesis of 4,4'-Dicarboxybenzanilide 4,4'-Dimethylbenzanilide (45.05 grams, 0.40 methyl equivalent) from A above, potassium permanganate (75.0 grams, 0.475 mole) and deionized water (1250 grams) are added to a reactor equipped with a reflux condenser and stirred with heating. After 46 minutes a reflux temperature of 105° C. is achieved and maintained. After an additional 68 minutes, all of the purple color caused by the potassium permanganate is gone, hence a second portion (37.5 grams, 0.2375 mole) of potassium permanganate added to the slurry. After an additional 60 minutes, the purple color induced by the potassium permanganate is again gone, hence a final portion (37.5 grams, 0.2375 mole) of potassium permanganate is added to the slurry. After an additional two hours at the 105° C. reaction temperature, heating ceases and the slurry is cooled to 50° C. The slurry is filtered through a pair of fritted glass funnels. The resultant clear, yellow colored filtrate is rotary evaporated under vacuum until a total volume of 800 milliliters is obtained. Concentrated hydrochloric acid (75 milliliters) is added to the stirred concentrated filtrate and the resultant precipitate is then recovered by filtration. The recovered precipitate is added to a beaker along with deionized water (750 milliliters), and the stirred contents are then brought to a boil. After cooling the aqueous slurry to 4° C. for twelve hours, a white crystalline product is filtered off and dried at 70° C. and 5 mm Hg in a vacuum oven to a constant weight of 11.03 grams. Fourier transform infrared spectrophotometric analysis of a potassium chloride pellet of the product confirmed the product structure of 4,4'-dicarboxybenzanilide (combined amide carbonyl and carboxylic acid carbonyl absorbance at 1689 cm$^{-1}$, amide N—H stretching absorbance at 3469 and 3323 cm$^{-1}$, carboxylic acid O—H stretching absorbances at 2984, 2825, 2665 and 2546 cm$^{-1}$. Differential scanning calorimetry of a portion (10.50 milligrams) of the product heated at 10° C. per minute under nitrogen flowing at 35 cubic centimeters per minute reveals a sharp melting point endotherm at 383.7° C.

C. Epoxidation of 4,4'-Dicarboxybenzanilide 4,4'-Dicarboxybenzanilide (9.98 grams, 0.070 —COOH equivalent from equivalent) from B above, epichlorohydrin (323.9 grams, 3.50 mole) and tetrabutylammonium chloride (0.1 gram, 1.0% wt. of the diacid reactant used) are added to a one liter glass round bottom reactor and heated to 80° C. with magnetically driven flowing at a rate of one liter per minute. After four hours at the 80° C. reaction temperature, infrared spectrophotometric analysis demonstrates incomplete conversion of the carboxylic acid groups (acid carbonyl absorbance at 1676 cm$^{-1}$; note: amide carbonyl absorbance overlays the acid carbonyl absorbance) to ester groups (ester carbonyl absorbance at 1722 cm$^{-1}$). At this time, the reaction temperature is decreased to 60° C. After 241 minutes at the 60° C. reaction temperature, Fourier transform infrared spectrophotometric analysis demonstrates complete conversion of the carboxylic acid groups to ester groups concurrent with the formation of a hazy, light amber colored solution. At this time, a water separator is interspersed between the reactor and the chilled (−2.5° C.) glycol condenser and an addition funnel containing sodium hydroxide (3.15 grams, 0.0788 mole) dissolved in deionized water (3.85 grams, 55% wt. of the solution) and a vacuum line are added to the reactor. The nitrogen purge is shut off simultaneously with initiation of the vacuum. The vacuum and reaction temperature are equilibrated at 84 mm Hg and 60° C., respectively and such that a vigorous reflux is maintained with continuous return of dry epichlorohydrin from the water separator to the reactor. After equilibration, dropwise addition of the aqueous sodium hydroxide commences accompanied by a gradual reduction in vacuum and reaction temperature. After 60 minutes, addition of the aqueous sodium hydroxide is complete and vacuum and reaction temperature are at 65 mm Hg and 55° C., respectively. After an additional 2 hours at the 65 mm Hg vacuum and 55° C. reaction temperature, heating ceases and the product slurry is cooled to 50° C. The recovered slurry is filtered under a nitrogen atmosphere and the resultant light amber colored solution rotary evaporated under a vacuum (2 mm Hg final conditions) at 90° C. for 45 minutes. The product is recovered as a viscous liquid. The liquid product is dissolved in methylene chloride (100 milliliters), then washed with deionized water (25 milliliters). The recovered methylene chloride layer is dried over anhydrous sodium sulfate, filtered, then the resultant filtrate rotary evaporated under a vacuum to a constant weight of 12.42 grams of viscous, light yellow colored liquid which solidified upon standing at room temperature (24° C.). Titration of a portion of the product reveals an epoxide equivalent weight of 207.64. Fourier transform infrared spectrophotometric analysis of a neat film of the product on a potassium chloride plate confirms the product structure for the diglycidyl ester of 4,4'-dicarboxybenzanilide (ester carbonyl absorbance at 1722 cm$^{-1}$, amide carbonyl absorbance at 1682 cm$^{-1}$, amide N—H stretching absorbance at 3449 and 3363 cm$^{-1}$, epoxide C—O stretching at 846 (852 slight shoulder) and 905 cm$^{-1}$).

D. Characterization of Crystallinity in the Diglycidyl Ester of 4,4'-Dicarboxybenzanilide Analysis of the diglycidyl ester of 4,4'-dicarboxybenzanilide from C above via crosspolarized light microscopy is completed using an optical microscope equipped with a programmable hot stage using a heating and cooling rate of 10° C. per minute. The results are reported in Table VI.

TABLE VI

CROSSPOLARIZED LIGHT MICROSCOPY ANALYSIS OF THE DIGLYCIDYL ESTER OF 4,4'-DICARBOXYBENZANILIDE

| Cycle Designation | Observed Transition Temperatures (°C.) | Comments |
| --- | --- | --- |
| First heating | 30[1] | [1]Birefringent semi-solid. |
|  | 40[2] | [2]First fluidity noted. |
|  | 47[3] | [3]Dispersed birefringent domains and opalescence observed. |
|  | 84[4] | [4]Isotropization. |
| First cooling | 9 | Opacity and birefringent morphology observed in semi-solid |

TABLE VI-continued

CROSSPOLARIZED LIGHT MICROSCOPY ANALYSIS OF THE DIGLYCIDYL ESTER OF 4,4'-DICARBOXYBENZANILIDE

| Cycle Designation | Observed Transition Temperatures (°C.) | Comments |
| --- | --- | --- |
|  |  | resin. |
| Second heating | 27[1] | [1]Fluidity and dispersed birefringent domains first observed. |
|  | 55[2] | [2]Birefringent domains increase in number. |
|  | 81[3] | [3]Isotropization. |
| Second cooling | 9 | Opacity and birefringent morphology observed in semi-solid resin. Crystallization noted after five minutes. |

EXAMPLE 8

A. Preparation of 4,4'-Dihydroxybenzophenone Oxime from 4,4'-Dihydroxybenzophenone 4,4'-Dihydroxybenzophenone (100.0 grams, 0.467 mole) is added to ethanol (300 milliliters) in a one liter Erlenmeyer flask and stirred. Once the 4,4'-dihydroxybenzophenone is in solution, a solution of hydroxylamine hydrochloride (48.6 grams, 0.699 mole) and sodium acetate (57.4 grams, 0.70 mole) in water (70 milliliters) is added to the flask, followed by additional ethanol (100 milliliters). The stirred mixture is heated on a hot plate to a gentle reflux (75° C.). After four hours at reflux, the stirred solution is cooled to room temperature and then filtered. The resultant filter cake is washed with ethanol (100 milliliters), then the total filtrate obtained (600.4 grams) concentrated to a weight of 219.2 grams by evaporation of part of the ethanol. The concentrated solution and deionized water (600 milliliters) are placed in a one liter Erlenmeyer flask and stirred. The addition of the deionized water induces the formation of a white precipitate. After thirty minutes of stirring, the slurry is filtered and the recovered white powder is dried in a vacuum oven to a constant weight of 98.22 grams. Fourier transform infrared spectrophotometric analysis of a potassium bromide pellet of the product confirms the product structure for 4,4'-dicarboxybenzophenone oxime (hydroxyl O—H stretching at 3400 cm$^{-1}$, aromatic C—O stretching at 1235 cm$^{-1}$, aromatic ring C—C stretching at 1607 and 1513 cm$^{-1}$). Differential scanning calorimetry of a portion of the product heated at 10° C. per minute under nitrogen flowing at 35 cubic centimeters per minute reveals a melting point endotherm at 155° C. followed by an exotherm (rearrangement of 4,4'-dihydroxybenzophenone oxime to 4,4'-dihydroxybenzanilide) at 155° to 188° C. Following this exotherm, a melting point endotherm for the rearrangement product is observed at 269° C. Liquid chromatographic analysis of a portion of the 4,4'-dihydroxybenzophenone product indicates a purity of 97.8%.

B. Preparation of 4,4'-Dihydroxybenanilide from 4,4'-Dihydroxybenzophenone Oxime 4,4'-Dihydroxybenzophenone oxime (66.0 grams, 0.288 mole) from A above and acetic acid (330 milliliters) are added to a 500 milliliter round bottom flask equipped with a stirrer, nitrogen purge, water cooled condenser and thermostatically controlled heating mantle. p-Toluenesulfonic acid catalyst (1.85 grams, 0.027 mole) is added to the stirred reaction mixture, and heating commences. After heating for two hours at 83° C., a precipitate formed. The reaction mixture is then stirred for an additional two hours at 87° C. and then diluted with deionized water (25 milliliters). Thirty minutes later, the contents of the reaction flask are transferred to a one liter Erlenmeyer flask and stirred. Immediately following this transfer, additional deionized water (400 milliliters) is added. The mixture is stirred for an additional 45 minutes, then filtered. The filter cake obtained is washed with deionized water (800 milliliters), then recovered and dried in a vacuum oven to a constant weight of 54.2 grams of light beige colored product. Fourier transform infrared spectrophotometric analysis of a potassium bromide pellet of the product confirms the product structure for 4,4'-dicarboxybenzanilide (amide N—H stretching absorbance at 3322 $cm^{-1}$, aromatic C—O stretching at 1251 $cm^{-1}$, aromatic ring C—C stretching at 1609 and 1514 $cm^{-1}$, amide carbonyl absorbance at 1646 $cm^{-1}$). Differential scanning calorimetry of a portion of the product heated at 10° C. per minute under nitrogen flowing at 35 cubic centimeters per minute reveals a sharp melting point endotherm at 273° C.

C. Preparation of an Advanced Resin Composition of the Diglycidyl Ester of 4,4'-Dicarboxybenzanilide with 4,4'-Dihydroxybenzanilide A portion (1.0479 grams, 0.00505 epoxide equivalent) of the diglycidyl ester of 4,4'-dicarboxybenzanilide from Example 7-C and a portion (0.2314 gram, 0.00202 —OH equivalent) of 4,4'-dihydroxybenzanilide from B above are dissolved in acetone (50 milliliters) containing tetrabutylphosphonium acetate-acetic acid complex (0.0036 gram, 0.34 phr based on the glycidyl ester reactant used). After mixing the solution for ten minutes, a homogeneous semi-solid mixture is recovered by evaporation of the acetone solvent. Differential scanning calorimetry analysis of a portion (29.4 milligrams) of the powder heated at 10° C. per minute under nitrogen flowing at 35 cubic centimeters per minute reveals an exotherm (156 joules per gram) between 100° C. and 230° C. A portion of the mixture is placed between two glass plates and heated directly to 100° C. at which point, an isotropic melt containing dispersed crystals is observed via optical microscopy (70× magnification) under crosspolarized light. After 2 hours at 100° C., the crystals present in the mixture cleared and a mobile, birefringent phase is observed. For the preparation of an advanced resin composition, the remaining mixture is transferred to an aluminum cup. The aluminum cup is placed in an oven which has been preheated to 100° C. After 2 hours at 100° C., the oven temperature is increased to 150° C. and maintained therein for 4 hours prior to cooling to room temperature (22° C.). After cooling to room temperature, an opaque solid is recovered from the aluminum cup. This solid exhibits a high level of phase birefringence when viewed by optical microscopy (70× magnification) under crosspolarized light. Differential scanning calorimetry of a portion of the solid using the aforementioned conditions reveals a pair of transition temperatures at 106° and 200° C.

EXAMPLE 9

Preparation of Cured Composition of the Diglycidyl Ester of 4,4'-Dicarboxybenzanilide Cured With 4,4'-Diaminobenzanilide 4,4'-Diaminobenzanilide (0.3319 gram, 0.00548 amine equivalent) is added to a portion (1.2128 grams, 0.00548 epoxide equivalent) of the diglycidyl ester of 4,4'-dicarboxybenzanilide from Example 7-C as a melt contained in an aluminum cup in an oven which has been preheated to 100° C. This mixture is periodically stirred over the next thirty minutes. After 12 hours at 100° C., the oven temperature is increased 20° C. per hour to a final temperature to 200° C. After six hours at 200° C., Differential scanning calorimetry analysis of a portion (14.4 milligrams) of the resin mixture heated at 10° C. per minute under nitrogen flowing at 35 cubic centimeters per minute reveals an exotherm (332 joules per gram) between 117° C. and 254° C. For the preparation of a cured casting, the resin mixture is maintained at the 100° C. temperature for four hours before increasing the temperature 20° C. per hour to a final temperature of 160° C. After six hours at 160° C., the oven is cooled to room temperature (22° C.) and a semi-translucent casting is recovered from the aluminum cup. The postcured casting exhibits dispersed birefringent regions having a liquid crystal type texture when viewed by optical microscopy (70× and 300× magnifications) under crosspolarized light. Differential scanning calorimetry of a portion (20.0 milligrams) of the casting using the aforementioned conditions reveals a glass transition temperature of 176° C.

EXAMPLE 10

Preparation of a Cured Composition of the Diglycidyl Ester of 4,4'-Dicarboxybenzanilide Cured With 4,4'-Diaminobenzanilide 4,4'-Diaminobenzanilide (0.1731 gram, 0.00305 amine equivalent) is added to a portion (1.0542 grams, 0.00508 epoxide equivalent) of the diglycidyl ester of 4,4'-dicarboxybenzanilide from Example 7-C as a melt contained in an aluminum cup in an oven which has been preheated to 100° C. This mixture is periodically stirred over the next thirty minutes. After 12 hours at 100° C., the oven temperature is increased 20° C. per hour to a final temperature to 200° C. After six hours at 200° C., the oven is cooled to room temperature (22° C.) and a semitranslucent casting is recovered from the aluminum cup. The postcured casting exhibits a low level of birefringence when viewed by optical microscopy (70× magnifications) under crosspolarized light. Differential scanning calorimetry analysis of a portion (20.0 milligrams) of the casting heated at 10° C. per minute under nitrogen flowing at 35 cubic centimeters per minute reveals a glass transition temperature of 180° C.

What is claimed is:

1. A composition comprising an essentially thermoplastic resin prepared by reacting a composition consisting essentially of
    (A) one or more polyglycidyl esters containing one or more mesogenic moieties, said polyglycidyl esters being those represented by either Formula I Formula I

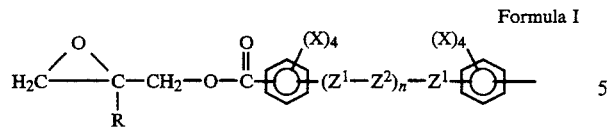

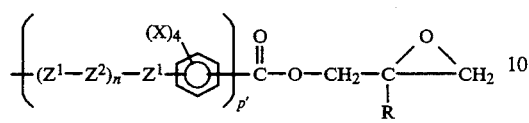

wherein at least about 80 percent of the —(Z$^1$-Z$^2$-)$_n$—Z$^1$— linkages and the glycidyl ester groups are in the pars position with respect to each other; each R and R$^1$ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, —NO$_2$, or —C≡N; each Z$^1$ is independently a direct single bond, —CR$^1$=CR$^1$—, —CR$^1$=CR$^1$—CR$^1$=CR$^1$—, —CR$^1$=N—N=CR$^1$—, —CR$^1$=CR$^1$—CO—O—(CHR$^1$)$_{p'}$—, —CR$^1$=CR$^1$—O—CO—(CHR$^1$)$_{p'}$—, —(CHR$^1$)$_{p'}$—O—CO—CR$^1$=CR$^1$—, —(CHR$^1$)$_{p'}$—CO—O—CR$^1$=CR$^1$—, —CR$^1$=CR$^1$—CO—O—, —O—CO—CR$^1$=CR$^1$—, —CO—NR$^1$—, —NR$^1$—CO—, —CO—NR$^1$—NR$^1$—CO—, —C≡C—, —C≡C—C≡C—, —CO—S—, —S—CO—, —CR$^1$=N—, —N=CR$^1$—, —O—CO—, —CO—O—, —CR$^1$=CR$^1$—CO—, —CO—CR$^1$=CR$^1$—, —CR$^1$=CR$^1$—O—CO—, —CO—O—CR$^1$=CR$^1$—, —CH$_2$—CH$_2$—CO—O—, —O—CO—CH$_2$—CH$_2$—, —N=N—,

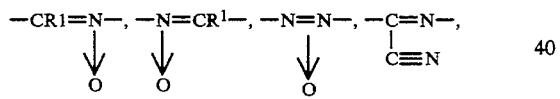

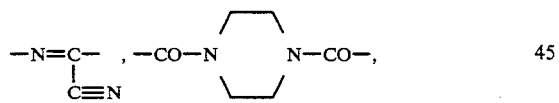

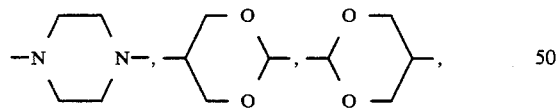

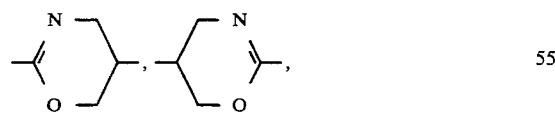

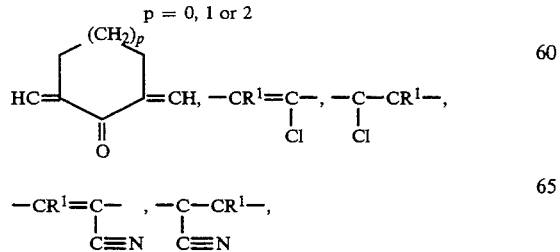

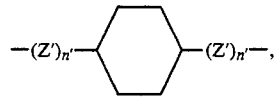

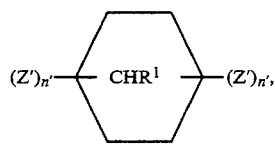

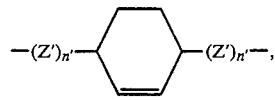

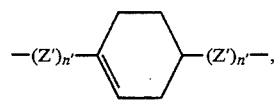

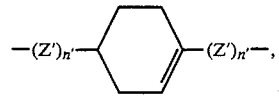

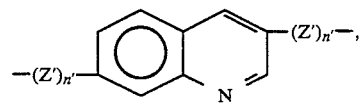

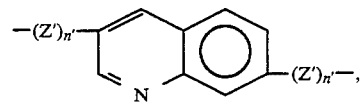

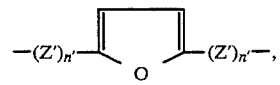

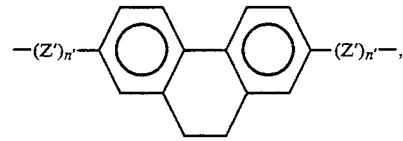

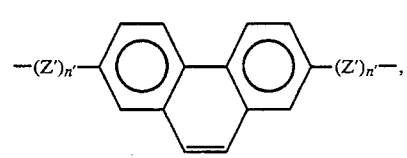

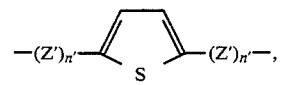

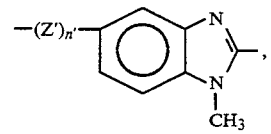

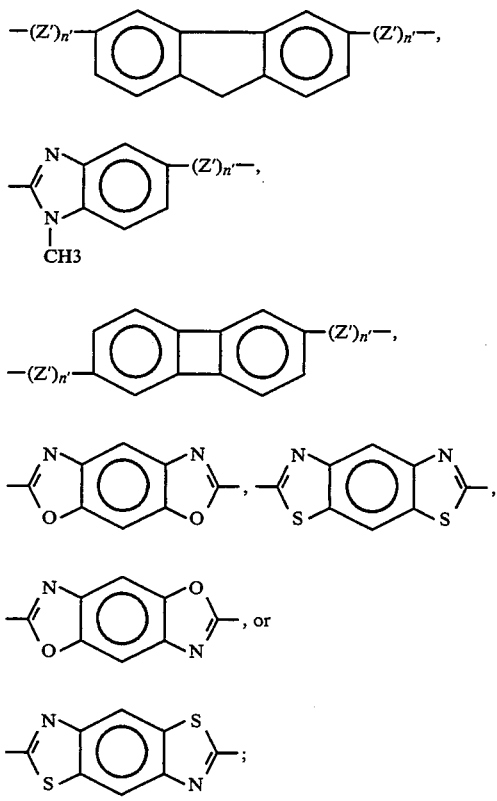

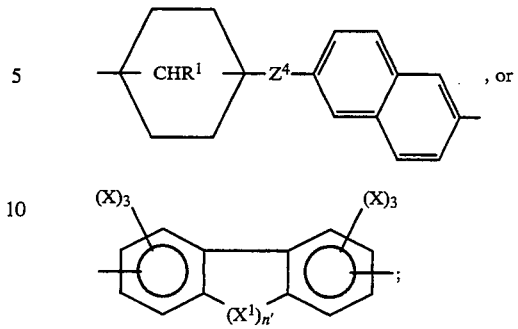

Z² is a group represented by a cyclic or bicyclic ring system containing from 5 to about 12 carbon atoms and is cyctoaliphatic, polycycloaliphatic, aromatic or a combination thereof; n is 0 to 2; each n' independently has a value of zero or one; p' is 1 or 2; p" has a value from zero to 100; add each Z' is independently a —CO—, —O—CO—, —CO—O—, —CO—NR¹—, or —NR¹—CO— group; or Formula II

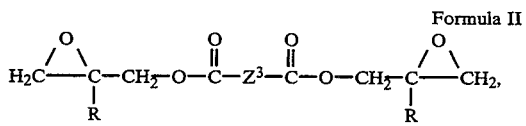

wherein Z³ is

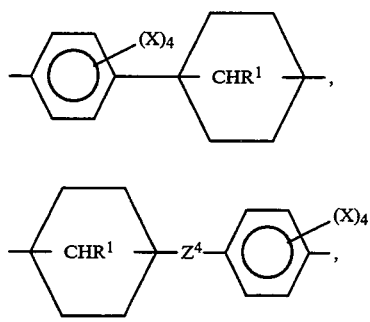

and Z⁴ is —CO—O—, —O—CO—, —NR¹—CO— or —CO—NR¹; X¹ is a divalent hydrocarbyl group having from 1 to about 10 carbon atoms which can contain one or more heteroatoms selected from N, O or S and is saturated or unsaturated; each R and R¹ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, —NO₂, or —C≡N; and n' is zero or one; with (B) at least one compound having an average of more than one active hydrogen atom per molecule selected from the group consisting of biphenols, and dicarboxylic acids;

wherein components (A) and (B) are meltable or soluble under conditions necessary for their derivatization or further reaction and are employed in quantitizes which provide a ratio of active hydrogen atoms per epoxide group of from about 0.96:1 to about 1.05:1.

2. An essentially thermoplastic resin of claim 1 wherein
(i) in component (A), when X is a hydrocarbyl or hydrocarbyloxy group it has from 1 to about 6 carbon atoms and when it is a halogen atom it is chlorine or bromine; and X¹ is a divalent hydrocarbyl group having from to about 4 carbon atoms; and
(ii) component (B) is a compound represented by the Formulas XVII or XVIII

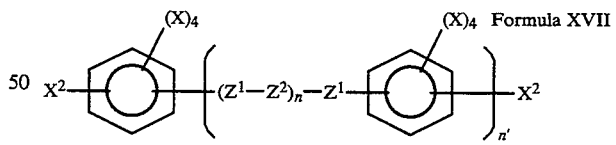

wherein each X is independently hydrogen, a hydrocarbyl or hydrocarbyloxy group having from 1 to about 12 carbon atoms, a halogen atom, —NO₂, or —C≡N; each Z¹ is independently a direct single bond, —CR¹=CR¹—, —CR¹=CR¹—CR=CR¹—, —CR¹=N—N=CR¹—, —CR¹=CR¹—CO—O—(CHR¹)-p'—, —CR¹=CR¹—O—CO—(CHR¹)p'—, —(CHR¹)-p'—O—CO—CR¹=CR¹—, —(CHR¹)-p'—CO—O—CR¹=CR¹—, —CR¹=CR¹—CO—O—, —O—CO—CR¹=CR¹—, —CO—NR¹—, —NR¹—CO—, —CO—NR¹—NR¹—CO—, —C≡C—, —C≡C—C≡C—, —CO—S—, —S—CO—, —CR¹=N—, —N=CR¹—, —O—CO—, —CO—O—, —CR¹=CR¹—CO—, —CO—CR¹=CR¹—, —CR¹=CR¹—O—CO—, —CO—O—CR¹=CR¹—, —CH₂—CH₂—CO—O—, —O—CH₂—CH₂—,
—N=N—,
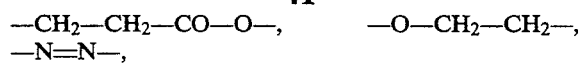
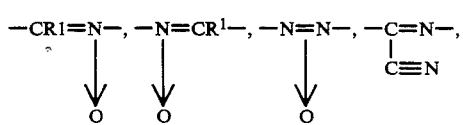
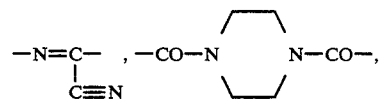
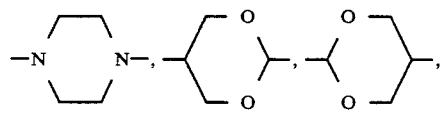
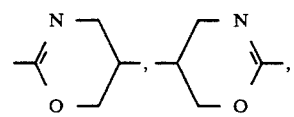
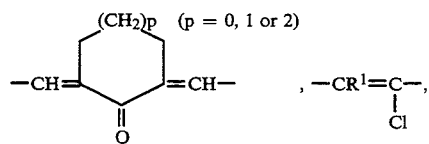
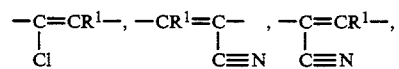
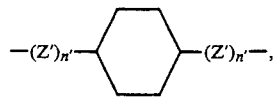
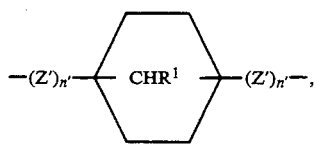
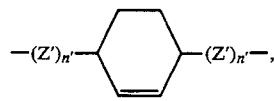
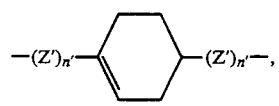
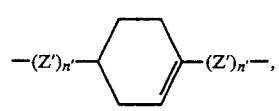
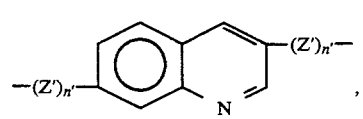
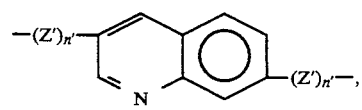
-continued
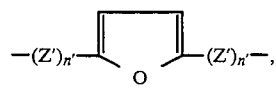
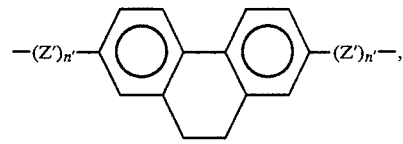
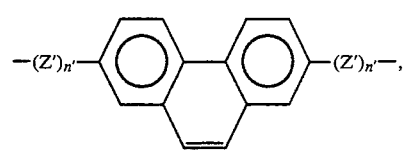
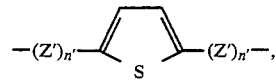
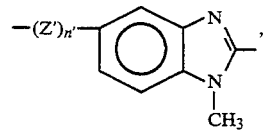
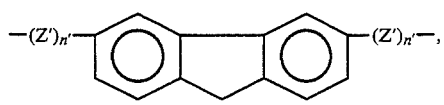
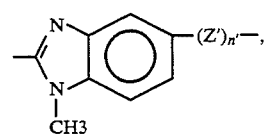
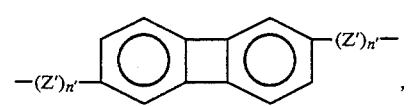
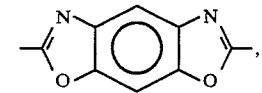
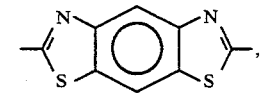
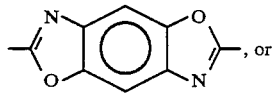
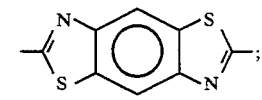
each $R^1$ is independently hydrogen or an aliphatic hydrocarbon group having from 1 to about 4 carbon atoms; $Z^2$ is a group represented by a cyclic or bicyclic ring system containing from 5 to about 12 carbon atoms and is cycloaliphatic, polycycloaliphatic, aromatic or a combination thereof; n is 0 to 2; each n' independently has a value of zero or one; p' is 1 or 2; each Z' is independently a —CO—, —O—CO—, —CO—O—, —CO—NR$^1$—, or —NR$^1$—CO— group; X$^2$ is independently a hydroxyl, or a carboxylic acid group.

3. An essentially thermoplastic resin of claim 2 wherein component (B) is hydroquinone, hisphenol A, 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachorobisphenol A, 3,3'-dimethoxybisphenol A, 4,4'-dihydroxybiphenyl, 4,4'-dihydroxy-α,α'-diethylstilbene, 4,4'-dihydroxy-α-methylstilbene, 4,4'-dihydroxybenzanilide, 4,4'-dihydroxy-2,2'-dimethylazoxybenzene, 4,4'-dihydroxy-α-cyanostilbene, bis(4-hydroxyphenyl)terephthalate, N,N'-bis(4-hydroxyphenyl)terephthalamide, bis(4'-hydroxybiphenyl)terephthatate, 4,4'-dihydroxyphenylbenzoate, bis(4'-hydroxyphenyl)-1,4-benzenediimine, 4,4''-dihydroxybiphenylbenzoate, 1,4-bis(4'-hydroxyphenyl-1'-carboxamide)benzene, 1,4-bis(4'-hydroxyphenyl-1'-carboxy)benzene, 4,4'-bis(4''-hydroxyphenyl-1''-carboxy)biphenyl, terephthalic acid, 4,4'-benzanilide dicarboxylic acid, 4,4'-phenylbenzoate dicarboxylic acid, 4,4'-stilbene dicarboxylic acid, 4,4'-dicarboxybiphenyl, 4,4'-dicarboxychalcone, 4,4'-dicarboxydiphenylazomethine, or any combination thereof.

4. An essentially thermoplastic resin of claim 2 wherein
 (i) component (A) is diglycidyl ester of 4,4'-stilbene dicarboxyiic acid or diglycidyl ester of 4,4'-dicarboxychalcone; and
 (ii) component (B) is 4,4'-stilbene dicarboxylic acid or 4,4'-dicarboxychalcone.

* * * * *

UNITED STATES PATENT AND TRADEMARK OFFICE
CERTIFICATE OF CORRECTION

PATENT NO. : 5,364,912
DATED : November 15, 1994
INVENTOR(S) : Robert E. Hefner, Jr. and Jimmy D. Earls It is certified that error appears in the above-identified patent and that said Letters Patent is hereby corrected as shown below:

In claim 1, column 37, line 16, "pars" should read --para--.

In claim 1, column 39, line 36, "cyctoaliphatic" should read --cycloaliphatic--.

In claim 1, column 40, line 33, "quantitizes" should read --quantities--.

In claim 2, column 40, line 44, after "from" insert --1--.

In claim 2, column 40, line 58, "-$CR^1$=$CR^1$-CR=$CR^1$-," should read -- -$CR^1$=$CR^1$-$CR^1$=$CR^1$-,--.

In claim 2, column 41, line 1, " -O-$CH_2$-$CH_2$-," should read -- -O-CO-$CH_2$-$CH_2$-,--.

In claim 3, column 43, line 9, "hisphenol A," should read --bisphenol A,--.

In claim 3, column 44, line 1, "terephthatate," should read --terephthalate,--.

Signed and Sealed this

Twenty-third Day of January, 1996

Attest:

BRUCE LEHMAN

Attesting Officer

Commissioner of Patents and Trademarks